(12) United States Patent
Takahashi et al.

(10) Patent No.: US 9,116,509 B2
(45) Date of Patent: Aug. 25, 2015

(54) RHYTHM BRAIN FITNESS PROCESSES AND SYSTEMS

(71) Applicant: LUMOS LABS, INC., San Francisco, CA (US)

(72) Inventors: Scott Takahashi, Stanford, CA (US); Karen Ladenheim, Los Altos, CA (US)

(73) Assignee: Lumos Labs, Inc., San Francisco, CA (US)

( * ) Notice: Subject to any disclaimer, the term of this patent is extended or adjusted under 35 U.S.C. 154(b) by 0 days.

(21) Appl. No.: 14/292,292

(22) Filed: May 30, 2014

(65) Prior Publication Data

US 2014/0352521 A1    Dec. 4, 2014

Related U.S. Application Data

(60) Provisional application No. 61/830,484, filed on Jun. 3, 2013.

(51) Int. Cl.
*G09B 15/00* (2006.01)
*G04F 5/02* (2006.01)

(52) U.S. Cl.
CPC .............. *G04F 5/025* (2013.01); *G09B 15/00* (2013.01)

(58) Field of Classification Search
CPC .................................. G09B 15/00; G04F 5/025
See application file for complete search history.

(56) References Cited

U.S. PATENT DOCUMENTS

| | | | | |
|---|---|---|---|---|
| 3,406,604 A | * | 10/1968 | Stickley et al. | 84/484 |
| 3,886,839 A | * | 6/1975 | del Castillo | 84/484 |
| 3,905,269 A | * | 9/1975 | Doerksen et al. | 84/470 R |
| 4,089,246 A | * | 5/1978 | Kooker | 84/470 R |
| 4,919,030 A | * | 4/1990 | Perron, III | 84/470 R |
| 5,231,661 A | | 7/1993 | Harnum et al. | |
| 5,267,734 A | | 12/1993 | Stamper et al. | |
| 5,417,137 A | * | 5/1995 | Krasny et al. | 84/484 |
| 5,421,236 A | * | 6/1995 | Sanger | 84/484 |
| 5,529,498 A | * | 6/1996 | Cassily et al. | 434/258 |
| 5,533,727 A | | 7/1996 | Demar | |

(Continued)

FOREIGN PATENT DOCUMENTS

| | | |
|---|---|---|
| JP | 2002222435 A | 8/2002 |
| KR | 20080013829 A | 2/2008 |

(Continued)

OTHER PUBLICATIONS

Baker, "Music Moves Brain to Pay Attention", (Stanford Study) (Aug. 5, 2007).

(Continued)

*Primary Examiner* — Robert W Horn
(74) *Attorney, Agent, or Firm* — Shartsis Friese LLP; Cecily Anne O'Regan

(57) ABSTRACT

Methods and systems for training cognitive skills are disclosed. The methods and systems include: providing, via a computing device and user interface display, musical rhythm training comprising at least one trial comprising: displaying on the user interface display, via the user computing device, a rhythm track comprising at least one stationary beat timing mark and at least one moving beat timing mark repeatedly moving along the rhythm track at a uniform speed; receiving via a user interface input an indication from the user that the user perceives a moving beat timing mark to be coincident with a stationary beat timing mark; and providing, via the user interface, an indicator that the user is correct or not correct.

28 Claims, 13 Drawing Sheets

(56) References Cited

U.S. PATENT DOCUMENTS

| | | | |
|---|---|---|---|
| 5,573,245 | A | 11/1996 | Weiner et al. |
| 5,683,082 | A | 11/1997 | Takemoto et al. |
| 5,709,604 | A | 1/1998 | Coats et al. |
| 5,882,258 | A | 3/1999 | Kelly et al. |
| 6,201,769 | B1 * | 3/2001 | Lewis ........................ 368/10 |
| 6,469,238 | B1 * | 10/2002 | Risley ...................... 84/470 R |
| 6,606,480 | B1 | 8/2003 | Pezzuti et al. |
| 6,632,174 | B1 | 10/2003 | Breznitz |
| 7,261,295 | B2 | 8/2007 | Grant |
| 7,358,432 | B2 * | 4/2008 | Risley ...................... 84/470 R |
| 7,540,615 | B2 | 6/2009 | Merzenich et al. |
| 7,557,287 | B2 * | 7/2009 | Wilson et al. ................. 84/484 |
| 7,722,501 | B2 * | 5/2010 | Nicolas et al. ................. 482/1 |
| 7,773,097 | B2 | 8/2010 | Merzenich et al. |
| 8,003,872 | B2 * | 8/2011 | Lopiccolo et al. ............ 84/609 |
| 8,051,376 | B2 * | 11/2011 | Adhikari et al. ............. 715/727 |
| 8,088,003 | B1 * | 1/2012 | Bickerton et al. ............ 463/30 |
| 8,154,227 | B1 | 4/2012 | Young et al. |
| 8,635,532 | B2 * | 1/2014 | Lengeling et al. ........... 715/725 |
| 8,821,242 | B2 | 9/2014 | Hinman et al. |
| 8,987,575 | B1 * | 3/2015 | Rossel ......................... 84/636 |
| 2003/0008270 | A1 | 1/2003 | Fleishman |
| 2003/0059759 | A1 | 3/2003 | Calhoun et al. |
| 2005/0053904 | A1 | 3/2005 | Shephard et al. |
| 2006/0003298 | A1 | 1/2006 | Hupert-Graff et al. |
| 2006/0292531 | A1 | 12/2006 | Gibson |
| 2007/0031798 | A1 | 2/2007 | Gottfried |
| 2007/0166675 | A1 | 7/2007 | Atkins et al. |
| 2007/0199431 | A1 * | 8/2007 | Kashioka ...................... 84/612 |
| 2007/0254270 | A1 | 11/2007 | Hersh |
| 2007/0299802 | A1 | 12/2007 | Kwok |
| 2008/0003553 | A1 | 1/2008 | Stark et al. |
| 2008/0003558 | A1 | 1/2008 | Chan et al. |
| 2008/0084427 | A1 | 4/2008 | Delahunt et al. |
| 2010/0041001 | A1 | 2/2010 | Delahunt et al. |
| 2010/0068684 | A1 | 3/2010 | Sabel |
| 2011/0097697 | A1 | 4/2011 | Tharanathan et al. |
| 2013/0072270 | A1 * | 3/2013 | Majchrowicz .................. 463/7 |
| 2013/0101975 | A1 | 4/2013 | Hardy et al. |
| 2013/0323704 | A1 | 12/2013 | Hinman et al. |
| 2014/0011556 | A1 * | 1/2014 | Kim et al. ....................... 463/7 |
| 2014/0031116 | A1 | 1/2014 | Hinman et al. |
| 2014/0227670 | A1 | 8/2014 | Sternberg et al. |
| 2014/0323190 | A1 | 10/2014 | Hinman et al. |
| 2014/0335487 | A1 | 11/2014 | Hinman et al. |
| 2014/0352521 | A1 * | 12/2014 | Takahashi et al. ............. 84/484 |

FOREIGN PATENT DOCUMENTS

| | | | |
|---|---|---|---|
| KR | 1020080038244 | A | 5/2008 |
| KR | 20080067055 | A | 7/2008 |
| KR | 20100051309 | A | 5/2010 |
| KR | 101000867 | B1 | 12/2010 |
| KR | 20120077540 | A | 7/2012 |
| WO | 2004006747 | A2 | 1/2004 |
| WO | 2009051284 | A2 | 4/2009 |
| WO | 2011028422 | A1 | 3/2011 |
| WO | 2011030337 | | 11/2011 |
| WO | 2012064999 | A1 | 5/2012 |
| WO | 2013180845 | A1 | 12/2013 |
| WO | 2014018313 | A1 | 1/2014 |
| WO | 2014127096 | A1 | 8/2014 |
| WO | 2014179278 | A1 | 11/2014 |
| WO | 2014186280 | A | 11/2014 |

OTHER PUBLICATIONS

Benikos, et al., "Short-term training in the Go/Nogo task: behavioural and neural changes depend on task demands". Int J Psychophysiol. 87 (3):301-312 (2013).

Cossins, "A Brain for Rhythm: A legendary rock and roll drummer teams up with a neuroscientist to explore the role of rhythm in brain function", The Scientist, Nov. 9, 2012.

Cuddy, et al., "Music, memory, and Alzheimer's disease: is music recognition spared in dementia, and how can it be assessed?", Medical Hypotheses 64(2):229-235 (2005).

Czerwinski, M., et al., "Automatization and Training in Visual Search", Amer. J. Psychol. 105, 271-315 (1992).

Donner, et al., "Involvement of the human frontal eye field and multiple parietal areas in covert visual selection during conjunction search," European Journal of Neuroscience 12(9) 3407-3414 (2001).

Duncan, et al., "Visual Search and Stimulus Similarity", Psychological Review 96(3) 4533-458 (1989).

Fischer, et al., "Effects of Daily Practice on Subitizing, Visual Counting, and Basic Arithmetic Skills", Optometry & Vision Development, 39(1) (2008).

Ho, et al., "Age, Skill Transfer, and Conjunction Search", Journal of Gerontology 57B(3) 277-287 (2002).

Ho, et al., "Plasticity of Feature-Based Selection in Triple-Conjunction Search", Canadian Journal of Experimental Psychology 57(1) 48-60 (2003).

Houben, et al., "Resisting temptation: Decreasing alcohol-related affect and drinking behavior by training response inhibition", Drug and Alcohol Dependence, 116(1), 132-136 (2011).

Lobley, et al., "Perceptual learning in visual conjunction search", Perception 27 1245-1255 (1998).

Logie, et al., "Cognitive processes in counting", Journal of Experimental Psychology: Learning, Memory, and Cognition, 13(2), 310 (1987).

Manuel, et al., "Brain Dynamics Underlying Training-Induced Improvement in Suppressing Inappropriate Action", J Neuroscience. 30(41):13670-13678 (2010).

Moreno et al., "ShortTerm Music Training Enhances Verbal Intelligence and Executive Function," Psychological Science (May 2011).

Muller, et al., "The functional neuroanatomy of visual conjunction search: a parametric fMRI study", NeuroImage 20, 1578-1590 (2003).

Ponds, et al., "Age differences in divided attention in a simulated driving task", J. Gerontology 43(6):151-156 (1988).

Railo, et al., "The role of attention in subitizing", Cognition, 107(1), 82-104 (2008).

Rueda, et al., "Training, maturation, and genetic influences on the development of executive attention", Proc. Natl Acad. Sci. 102(41):14931-14936 (2005).

Treisman, et al., "A feature-integration theory of attention", Cognitive Psychology 12 97-136 (1980).

Funny Games, Grid Memory, Aug. 21, 2011, http://www.funny-games.biz/grid-memory.html.

Improvememory.org, Memory Games, Mar. 12, 2012, http://www.improvememory.org/games.

Softschools.com, Path Memory, Nov. 4, 2011, http://www.softschools.com/games/memory_games/path_memory/.

Papaioannidis, 'Clockwork Brain—The best iPad and iPhone puzzle game is now available!', Applecasts (Feb. 20, 2012) (http://www.applecasts.com/clockwork-brain-best-iphone--puzzle-game).

Anvari, et al., "Relations among musical skills, phonological processing, and early reading ability in preschool children", J. Experimental Child Psychology 83:111-130 (2002).

Chan, "Rhythm Action Tap Sonic Offline (New Love Ritmo Theme)," http://freegalaxytip.blogspot.kr/2012/rhythm-action-tap-sonic-offlinenew-love.html (Dec. 13, 2012).

Crone, "Neurocognitive Development of Rational Reasoning", Dev. Sci. 12(1): 55-56 (2009).

Daneman, et al., "Individual differences in working memory and reading", Journal of Verbal Learning and Verbal Behavior 19(4): 450-466. doi:10.1016/S0022-5371(80)90312-6 (1980).

Ekstrom, et al., "Manual for Kit of Factor-Referenced Cognitive Tests," pp. 173-179, Princeton NJ: Educational Testing Service (1976).

Ira, "Track my train app review" Top Apps http://www.topapps.net/blackberry/track-my-train-app-review.html (Feb. 26, 2013).

Jaeggi, et al., "Improving fluid intelligence with training on working memory", Proc. Nat'l Acad. Sci., 105(19):6829-6833 (2008).

Ji et al., "Design and implementation of cognitive enhancement games for rehabilitation of old mans", Korea Info. Sci. Soc. J. 14: 239-246 (2008).

(56) References Cited

OTHER PUBLICATIONS

Kane, et al., "The role of prefrontal cortex in working-memory capacity, executive attention, and general fluid intelligence: An individual-differences perspective" Psychonomic Bulletin & Review 9(4), 637-671, doi:10.3758/BF03196323 (2002).

Karbach, "How useful is executive control training? Age differences in near and far transfer of task-switching training", Developmental Science, 12: ,978-990 (2009).

Lumos Labs, Addition Storm.

Mack, "Pulse: volume One Steps into Rhythm Games with Original Music", Inside Mobile Apps, (May 13, 2011).

Matzen, et al., "Recreating Raven's Software for Systematically generating large numbers of Ravin-like matrix problems with normed properties," Behavior Research Methods 42(2):525-541 (2010).

Nicologic; (https://webarchive.org/web/2008111113191/http://www.nicologic.fr/index.php? LANGUE=ENG&MENU=MAIN) Nov. 11, 2008.

Nosek, et al., "The go/no-go association task", Social Cognition 19(6):625-666 (2001).

Rajender et al., "Efficacy of cognitive retraining techniques in children with attention deficit hyperactivity disorder", German J. Psychiatry 14(2):55-60 (2011).

Rogers, "The cost of a predictable switch between simple cognitive tasks", Journal of Experimental Psychology: General, 124:207-231 (1995).

Shepard, et al. "A Chronometric Study of Mental Paper Folding," Cognitive Psychology, 3(2):228-243 (1972).

Sheridan, "Review: candy train-full steam ahead", posted in Endless, Games, iPad, iPhone (2011); http://applenapps.com/review/candy-train#,VEXvrSKsUcY.

Sohlberg, "Effectiveness of an attention-training program," J Clin Exp Neuropsychol 9 (2):117-30 (1987).

Stroop, "Studies of interference in serial verbal reactions", J. of Exp. Psych. 18 (6):643-662 (1935).

Turner, et al., "Is working memory capacity task dependent?", J. Memory and Language, 28(2):127-154. (1989).

\* cited by examiner

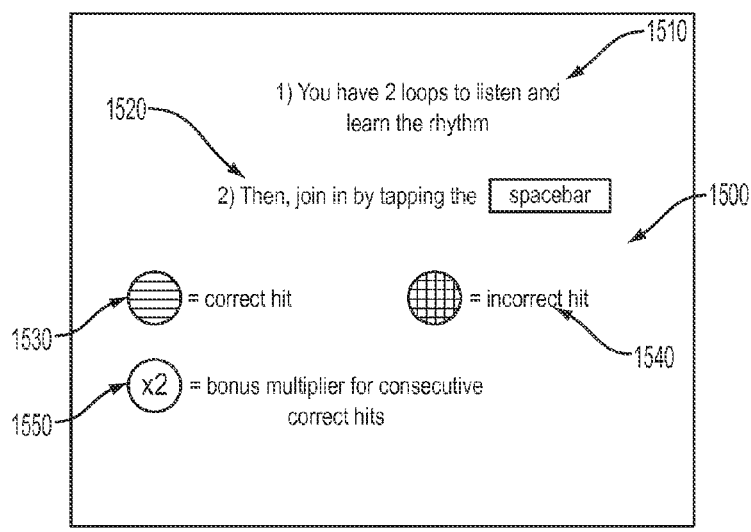
FIG. 15
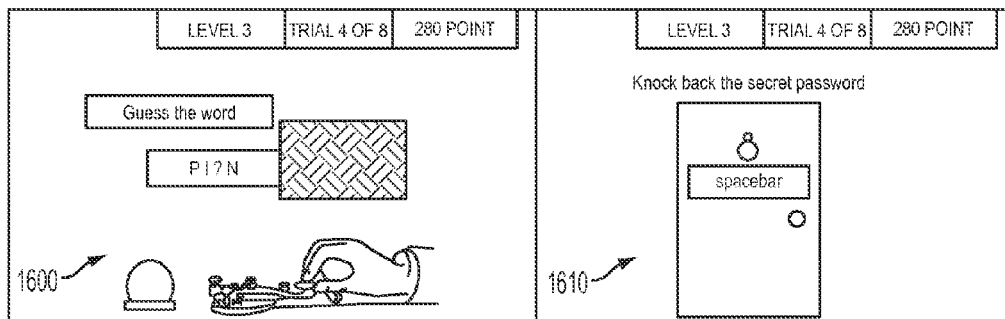
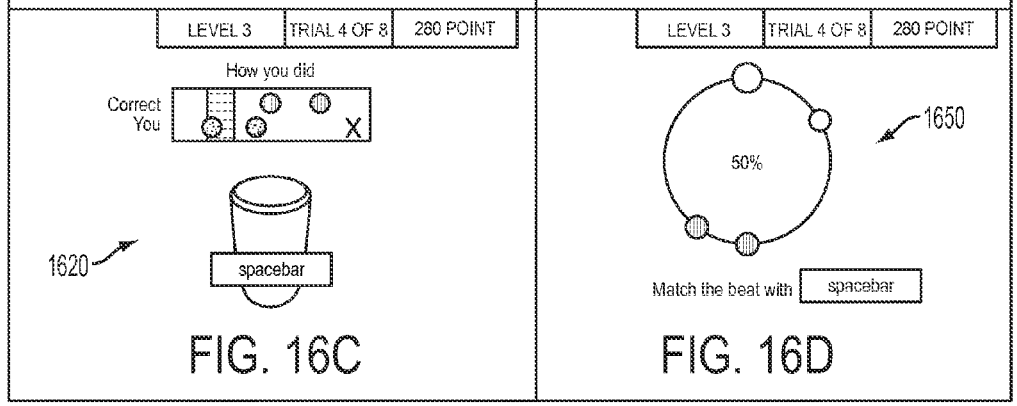

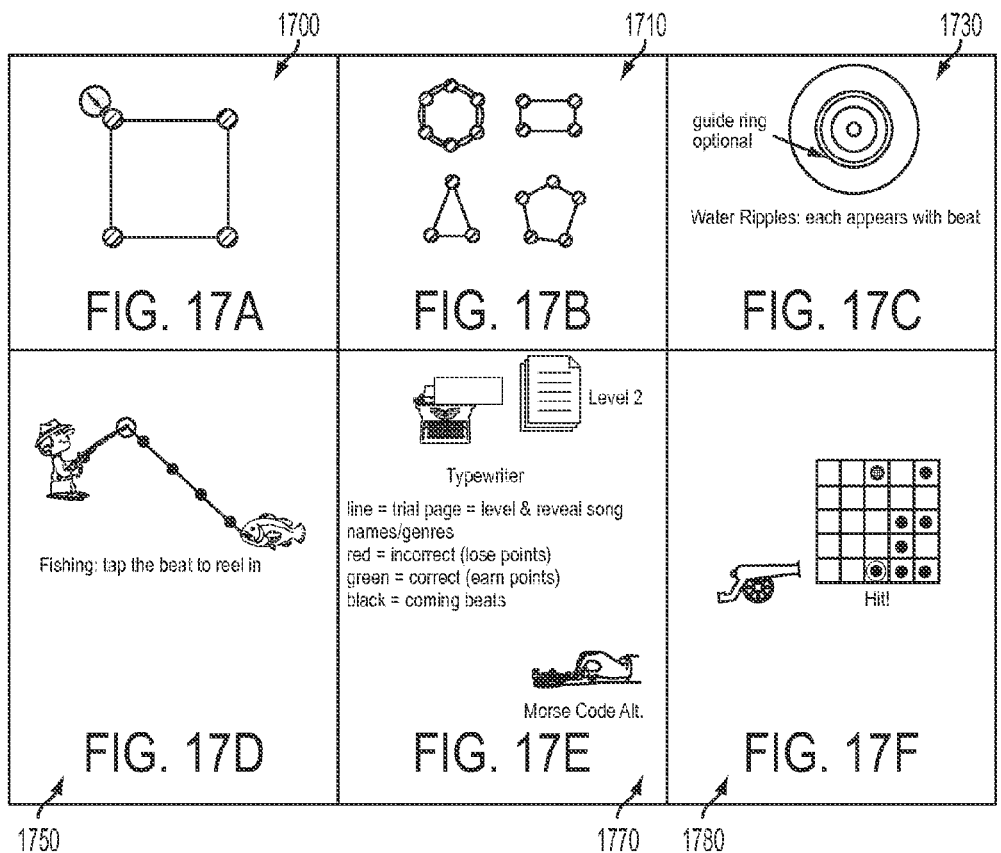

RHYTHM BRAIN FITNESS PROCESSES AND SYSTEMS

CROSS-REFERENCE

This application claims priority to U.S. Provisional Patent Application Ser. No. 61/830,484, entitled, RHYTHM BRAIN FITNESS PROCESS AND SYSTEMS filed on Jun. 3, 2013, which is incorporated herein by reference in its entirety.

BACKGROUND OF THE INVENTION

Scientific studies have revealed links between musical skills, including rhythm, and cognitive performance in areas such as attention, perception, working memory, speech, and language. Among other theories as to why, it is possible that the intense concentration and flow in musical skill development, along with the deep levels of passion and engagement in that development, contribute to improvements in other cognitive skill areas. As examples, see: Pedia Staff Blog, August 2011, *Music Therapy and Speech Language Pathology—A Collaboration* (Parts 1 & 2, Rachel See Smith, M A, MTBC, Board Certified Music Therapist, http://www.pediastaff.com/blog/guestblogmusictherapyand-speechlanguagepathologyacollaborationparts124364; *How arts Training Improves Attention and Cognition*, Michael I. Posner and Brenda Patoine, Sep. 14, 2009, http://dana.org/news/cerebrum/detail.aspx?id=23206; *Music Moves Brain to Pay Attention* (Stanford Study), Mitzi Baker, Aug. 5, 2007, http://www.sciencedaily.com/releases/2007/08/070801122226.htm; *A Brain for Rhythm: A legendary rock and roll drummer teams up with a neuroscientist to explore the role of rhythm in brain function*, The Scientist, Dan Cossins, Nov. 9, 2012, http://www.thescientist.com/?articles.view/articleNo/33213/title/ABrainforRhythm/; *Music, memory, and Alzheimer's disease: is music recognition spared in dementia, and how can it be assessed?*, Lola L. Cuddy and Jacalyn Duffin, Medical Hypotheses, Volume 64, Issue 2 (2005), Pages 229-235, http://www.sciencedirect.com.ezproxy.stanford.edu/science/article/pii/S0306987704005158; *ShortTerm Music Training Enhances Verbal Intelligence and Executive Function*, Moreno et al., Psychological Science, May 2011, http://pss.sagepub.com/content/22/11/1425.

This research suggests that regular use of a rhythm training game could help users experience cognitive benefits. A variety of music-related games are available on the market, which have been shown to be quite popular, but while they may be fun and engaging, they are not designed to improve cognitive abilities. Accordingly, the present application discloses a method and apparatus for the utilization of rhythmic training in the form of a rhythm training game for purposes of user cognitive skill development. The engaging game involves a musical skill, such as rhythm, without requiring the user to engage in actually learning to play and playing a musical instrument or learning to read and reading music. The game becomes adaptively more difficult as the individual improves by utilizing more complex musical or rhythmic skills or rhythms.

SUMMARY

A method and apparatus for training a cognitive skill are disclosed which may comprise: providing, via a user computing device user interface display, musical rhythm training with at least one trial comprised of: displaying on the user interface display, via the user computing device, a rhythm track comprising at least one stationary beat timing mark and at least one moving beat timing mark repeatedly moving along the rhythm track; receiving via a user interface input an indication from the user that the user perceives a moving beat timing mark to be coincident with a stationary beat timing mark; and providing, via the user interface, an indicator that the user is correct or not correct. The method and apparatus may further comprise the rhythm track comprising a circle, a straight line, or a polygon, which may be an equilateral polygon.

The stationary beat timing mark and the moving beat timing mark may be distinguishable from each other by at least one of composition and color. The moving beat timing mark may be rendered invisible to the user, requiring the user to determine whether the moving beat timing mark and stationary beat timing mark are coincident based on the user's memory of prior moving beat timing marks and the user's rhythmic skill.

The rhythm track may comprise a plurality of rhythm tracks, each of which may comprise at least one stationary beat timing mark and at least one moving beat timing mark repeatedly moving along the respective rhythm track at a speed. The plurality of rhythm tracks may comprise tracks which are made more challenging by adjusting one of speed, number, and pattern of moving beat timing marks.

The plurality of rhythm tracks may comprise a left hand rhythm track and a right hand rhythm track; and the method and apparatus may comprise providing a correct rhythm beat timing indicator on a respective stationary beat timing mark when the user indication is coincident with the stationary beat timing mark on one of the respective right hand rhythm track and left hand rhythm track.

INCORPORATION BY REFERENCE

All publications, patents, and patent applications mentioned in this specification are herein incorporated by reference to the same extent as if each individual publication, patent, or patent application was specifically and individually indicated to be incorporated by reference, for all purposes and as if the entire publication, patent or patent application were repeated in the present application verbatim, including any specification, claims and drawing. Such documents would include the articles referenced above and patents and publications of interest to the field.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosed subject matter and its operation are utilized, and the accompanying drawings of which:

FIG. 15 shows a tutorial screen display according to aspects of the disclosed subject matter;

FIGS. 16A-D show possible screen displays for variations on displaying rhythm feedback and receiving rhythm input from the user, according to aspects of the disclosed subject matter; and FIGS. 17A-F show possible screen displays for variations on displaying rhythm feedback and receiving rhythm input from the user, according to aspects of the disclosed subject matter.

DETAILED DESCRIPTION OF THE INVENTION

Figure 1:
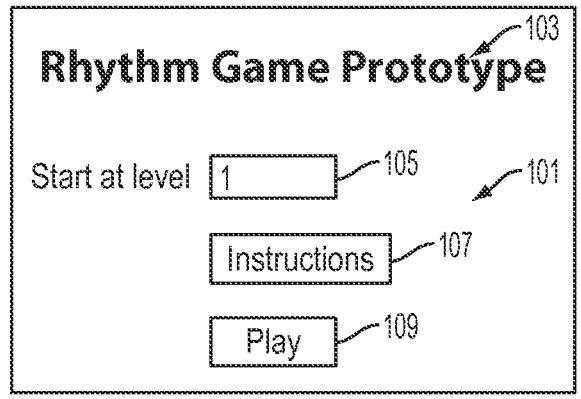
FIG. 1 shows a game start screen display according to aspects of the disclosed subject matter.

Computer-based video games can be both fun and serve to train cognitive abilities, and aspects of embodiments of the disclosed subject matter describe games that utilize, challenge, and develop musical and rhythm skills to enhance cognitive skills more generally. Even non-musician adults can possess enough music skills to perform the proposed game(s) for the desired training, which is preferable because such adults can achieve the cognitive benefits from the training without having to first try to learn to play or read music.

According to aspects of embodiments of the disclosed subject matter, a game is proposed that is focused on one musical fundamental, such as rhythm. The proposed rhythm cognitive training game is simple enough to learn and interact with that it can lower the barrier to entry for adults to engage with music in a more quick and rewarding manner. Additionally, the skills utilized as a user improves at the game have the potential to teach the user tangible rhythm skills, that can serve to improve understanding and increase coordination outside of the game. For example, it can help the user engage with others socially through music in everyday situations, such as listening to music, clapping/tapping to music, and dancing. Ultimately, these positive effects can increase the satisfaction of the user with the game and further the ultimate cognitive skill training objective.

The proposed game utilizes an intuitive design that is user friendly and that can include basic entry levels to make the game easy to initially learn, which may be especially important for older adults and non-musicians. The game can have adaptively challenging levels with faster or more complex rhythms that continuously challenges the user's abilities as the user improves.

In at least some configurations, a user operates a computing device that executes a browser to operate the proposed game, which can connect to a server via a computer network. The computing devices include, but are not limited to, personal computers, digital assistants, personal digital assistants, cellular phones, mobile phones, tablets, smart phones or laptop computers. The network is typically the Internet, but can also be any network, including but not limited to any combination of a LAN, a MAN, a WAN, a mobile, wired or wireless network, a private network, or a virtual or ad hoc private network. As will be understood very large numbers (e.g., millions) of users are supported and can be in communication with the website at any time.

The browser can include any application that allows users to access the World Wide Web. Suitable applications include, but are not limited to, Microsoft Internet Explorer®, Netscape Navigator®, Mozilla® Firefox, Apple® Safari or any application capable of or adaptable to allowing access to web pages on the World Wide Web.

In at least some configurations the user can access the rhythm cognitive skill training application as a downloaded application on a computing device, such as an "app" available through the Apple App Store.

The disclosed subject matter can be understood in part with reference to FIG. 1, which shows an example of a game start screen display 101 according to aspects of the disclosed subject matter. The screen display 101 of FIG. 1 can have a title bar 103, a level selection entry box 105, an instructions selection button 107 and a play selection button 109.

Figure 2:
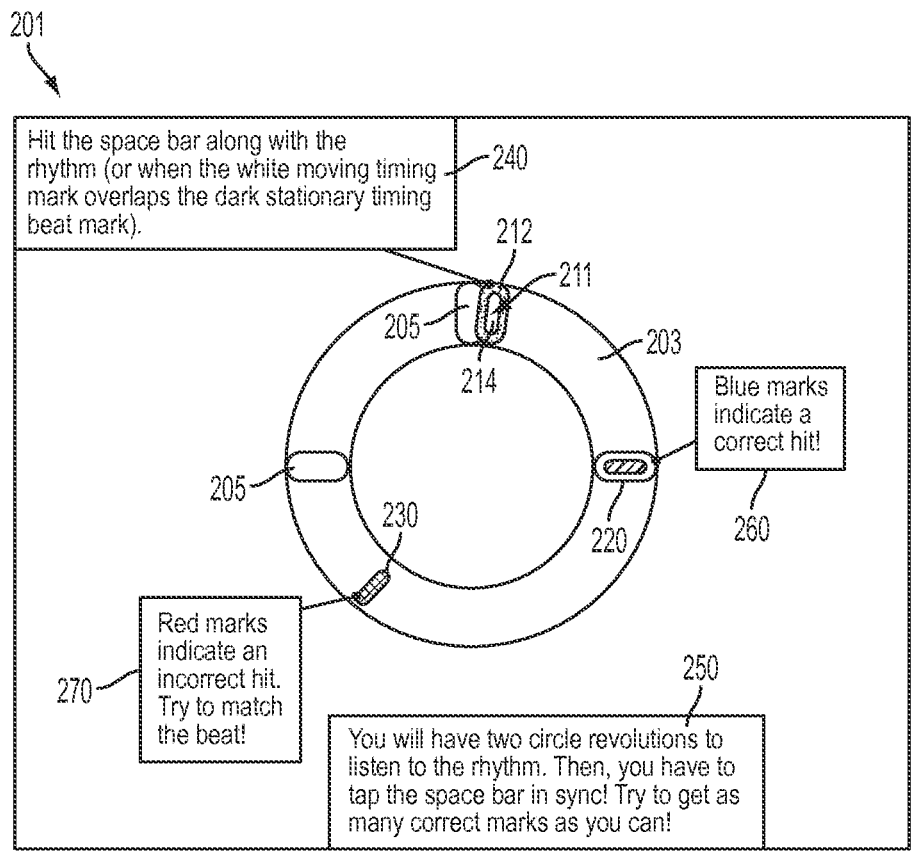
FIG. 2 shows a game tutorial screen display according to aspects of the disclosed subject matter.

FIG. 2 is a game tutorial screen display 201 according to aspects of the disclosed subject matter. The screen display 201 can include a rhythm track 203, which can be circular. At least one stationary beat mark 205, which can in one embodiment be an oval stretching across the width of the rhythm track 203. A white moving timing mark 211, which may also be an oval stretching across the width of the rhythm track 203, may have a moving timing mark periphery 212 and a moving timing mark sweet spot 214. It will be understood that the moving rhythm timing mark 211 travels around the rhythm track 203 at a speed according to the beat of the rhythm. Assuming the movement of the moving rhythm timing mark 211 around the rhythm track 203 corresponds to one measure of the music for which the rhythm is taken, then the measure, according to music notation, e.g., a 4/4 notation indicates four beats per measure and each beat equaling a quarter note.

Thus, for example, four quarter notes occurring in a measure can be indicated by stationary rhythm timing (beat) marks 205 at each of the cardinal points on the track 203, i.e., north, east, south and west. Similarly two half notes in the measure can be represented by a stationary beat mark 205 in the north position and one in the south position. Eighth notes can be represented by a stationary beat mark 205 following another stationary beat mark in a cardinal position at one of the intermediate positions such as north east after north, south east after east, south west after south and northwest after west. That is the eighth note can be indicated to start at the cardinal west point, as an example, and end on the non-cardinal northwest point. Similarly four sixteenth notes can be represented by four stationary beat marks 205 at the north, north-by-northeast, northeast and east-by-northeast positions on the track 203, each of these being separated by a sixteenth of the distance around the circle of the compass points. Specifically, the rhythm or beat represented by the rhythm track 203 in FIG. 2 for a 4/4 measure could correspond to a quarter note (at the north position), followed by a half note at the east position and a quarter note at the west position, as the moving rhythm marker 211 travels around the rhythm track 203 in time with each measure represented by such a circumnavigation. That is, assuming duration is part of the input of the user, there is a continuous input from the east point to the west point and a continuous input from each of the north point to the east point and from the west point to the north point. Alternatively the user may simply be required to track and reproduce the initiation points of the notes, i.e., tap the space bar as an example at the concurrence of the moving rhythm timing marker 211 with each of the north, east and west points as illustrated in FIG. 2.

As can also be seen with regard, e.g., to FIG. 2, a system and method according to the disclosed subject matter can generate a correct perception indication mark 220, e.g., when the computing device receives an input, e.g., from the user depressing a user interface element, such as, a keyboard space bar, e.g., in timing with the moving rhythm marker 211 crossing a stationary rhythm marker 205. An incorrect perception indication mark 230 may also be created by the computing device when the computing device detects that the user has entered the input at a wrong time. That is, e.g., the user has made an input when the moving rhythm marker 211 was not coincident with a stationary rhythm marker 205.

It will be understood that, as shown in FIG. 2, the moving rhythm marker 211 may be coincident with the stationary rhythm marker 205, so as to be completely coincident with the stationary rhythm marker 205, i.e., to have the moving timing marker periphery 212, along with the moving timing mark sweet spot 214 both completely overlying the stationary rhythm marker 205. Alternatively, in some embodiments, the moving timing mark sweet spot 214 alone may need to be completely overlying the stationary rhythm marker 205 and still be considered to be a correct input. Additionally, in some embodiments, having any portion of the moving rhythm marker 211 overlying the sweet spot of or, alternatively, any other portion of the stationary rhythm marker 205 may be considered a correct input. These variations in the nature of a correct input by the user may also depend on the user attained level and/or the number of the completed trials within a level, etc. As discussed further below, these forms of coincidence with the stationary rhythm marker 205 may also be scored differently for purposes of evaluating the performance of the user, from only the complete coincidence being considered a correct response to the others being considered correct, but scored with a lower score.

As can be seen in FIG. 2 the screen display 201 may also include a variety of instructional text displays, such as text box 240 "Hit the space bar along with the rhythm (or when the white moving timing mark overlaps with the dark stationary beat mark)," text box 251 "You will have two circle revolutions to listen to the rhythm. Then, you have to tap the space bar in sync! Try to get as many correct marks as you can!," text box 260 "Blue marks indicate a correct hit!" and text box 270 "red marks indicate an incorrect hit. Try to match the beat!" These can be displayed temporarily at the beginning of the game or round of play or other time; for example, to remind a user not scoring very well, and then fade out while actual play is ongoing.

According to aspects of the disclosed subject matter, audio signals may be generated by the computing device implementing the system and method according to the disclosed subject matter. As an example, an audio clave can sound to set the tempo. This can be with the display showing the rhythm track 203 alone or with the moving rhythm marker 205 traveling around the rhythm track 203 and covering the stationary rhythm markers 205. The beats could be the number of beats per measure, and could sound only in coincidence with a stationary rhythm marker 205 or for each beat in the measure, even if a corresponding note of one or more beats does not start on that position in the rhythm track 201. The word "LISTEN" can appear on the screen display 300.

Figures 3A, 3B:
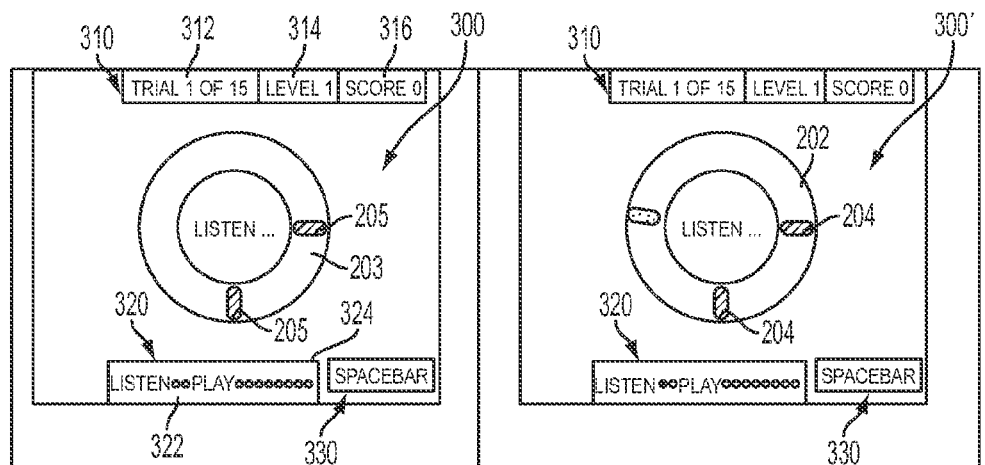
FIGS. 3A-3D show game mechanics screens according to aspects of the disclosed subject matter.
Figures 3C, 3D:
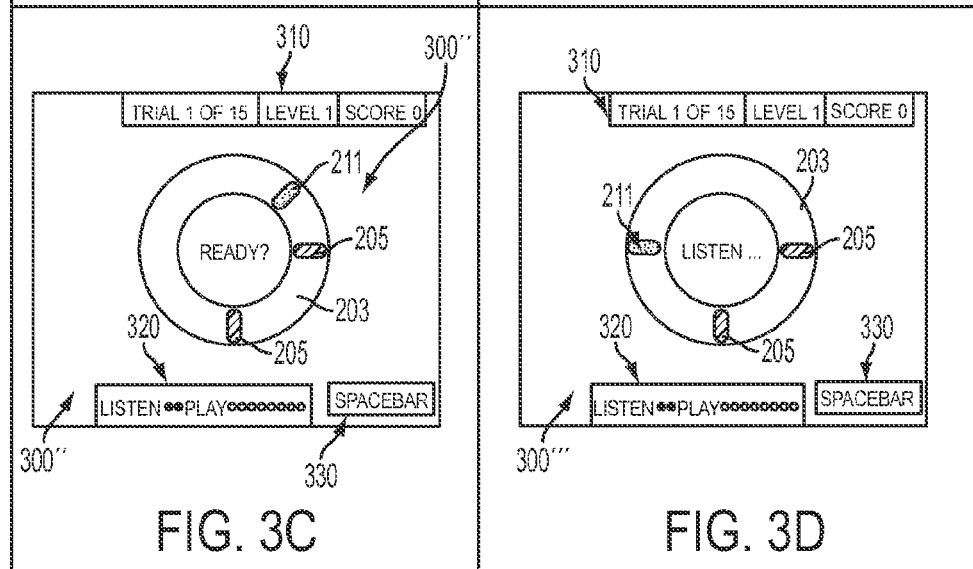

As shown on the screen display 300' of FIG. 3B the white oval moving rhythm marker 211 can circle the rhythm track 203 as the trial rhythm plays aurally. Rhythms may be played using a variety of instrumental percussion sounds chosen randomly at the start of each trial. Sounds can include a bongo drum, a shaker, a conga, a snare, a hand-drum, a tambourine, a cowbell, etc. A first black circle under the "LISTEN" bar at the bottom of the screen display 300', in a game trial status bar 320 can be filled. As shown in FIG. 3C at the start of the second "LISTEN" loop, the word "LISTEN" is replaced by "READY?" The second black circle under the "LISTEN" bar at the bottom of the screen display 300", on the game trial mode status bar 320 is filled. As seen in the screen display 300', as seen in FIG. 3D, as an example, after the moving rhythm marker 211 makes one half loop after the second "LISTEN" loop, the word "READY?" can be replaced with is replaced by the word "PLAY!" Scoring can them begin, e.g., when the white oval moving rhythm marker 211 reaches the top of the rhythm track circle 203.

It will also be seen that the screen displays 300, 300', 300" and 300'" of FIGS. 3A, 3B, 3C and 3D can have a game trial status bar 310, which can include a trial number indication 312, a level indicator 314 and a score display 316. The screen displays 300, 300', 300" and 300'" of FIGS. 3A, 3B, 3C and 3D can have a game mode status bar 320, which can indicate listen mode 322 and play mode 324. Also the 300, 300', 300" and 300' of FIGS. 3A, 3B, 3C and 3D can have a virtual spacebar button 330, which, on, e.g., touch screen displays, can act as the spacebar the user is to depress, by, in this case, taping the virtual spacebar.

Figures 4A, 4B:
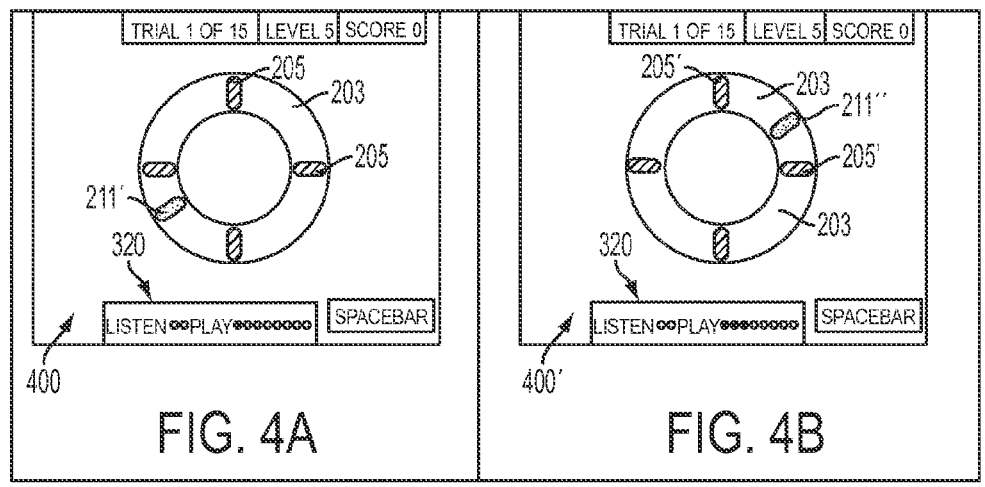
FIGS. 4A-C show game mode change screen displays according to aspects of the disclosed subject matter.
Figure 4C:
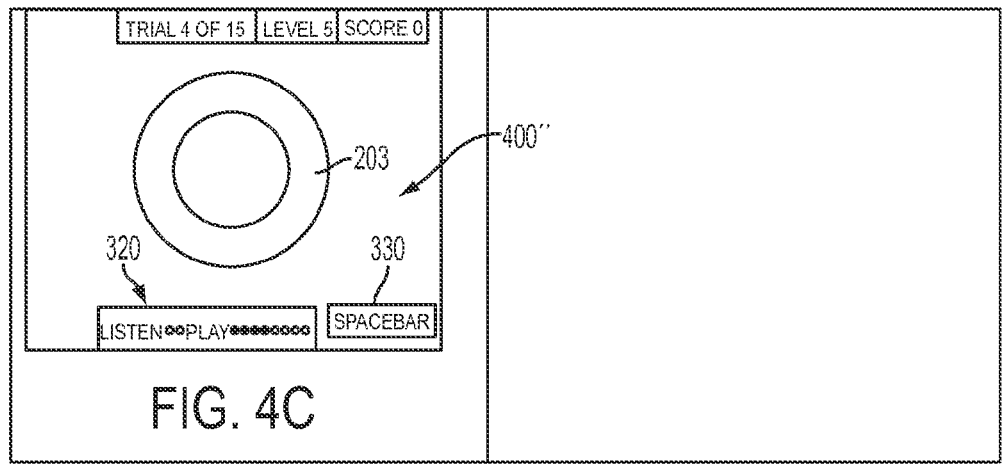

Turning to FIGS. 4A-4C, variable trial game play modes can be seen. In FIG. 4A, the normal game play mode as discussed above can be seen, with the game mode status bar 320 indicating at 324 that play mode is in operation and this is the first trial being played by the user. At this point, as an example, and depending on the level of the user, as indicated in FIG. 4B, the stationary rhythm markers 205' and/or the moving rhythm marker 211' may become faded or flashing or change color, or the like, as an indication that the normal playing mode is about to change. As can be seen from the screen display 400" of FIG. 4C, the stationary rhythm timing markers can completely disappear along with the moving rhythm timing markers and the user can be left to remembering the rhythm and beat from memory.

Figure 5:
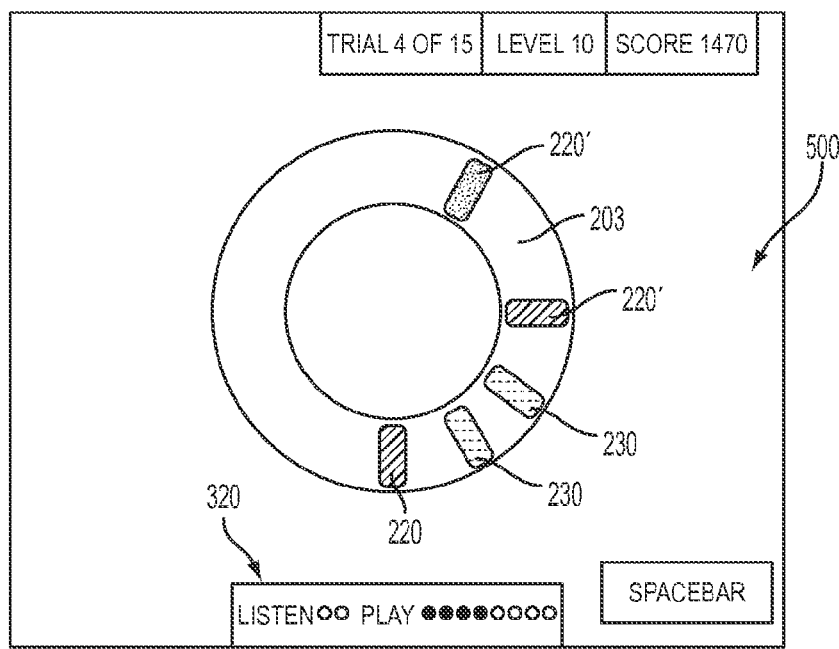
FIG. 5 shows a further game mechanics screen display according to aspects of the disclosed subject matter.

FIG. 5 illustrates, by way of example, red visual oval feedback indicators 230 that can be utilized to signify an incorrect hit. These may also be accompanied by a negative feedback sound, which can in some embodiments remain consistent throughout the game, either as to the appearance of the incorrect input indicators and/or the occurrence of the aural incorrect input indicator. Blue visual oval feedback indicators 220 can be utilized to signify a correct hit and may or may not also be accompanied by an additional audio indicator. Since, in some embodiments, the computing device can constantly play the correct rhythm, an audio indicator may not be needed for the user achieving the correct input timing for the rhythm being played.

Figure 6:
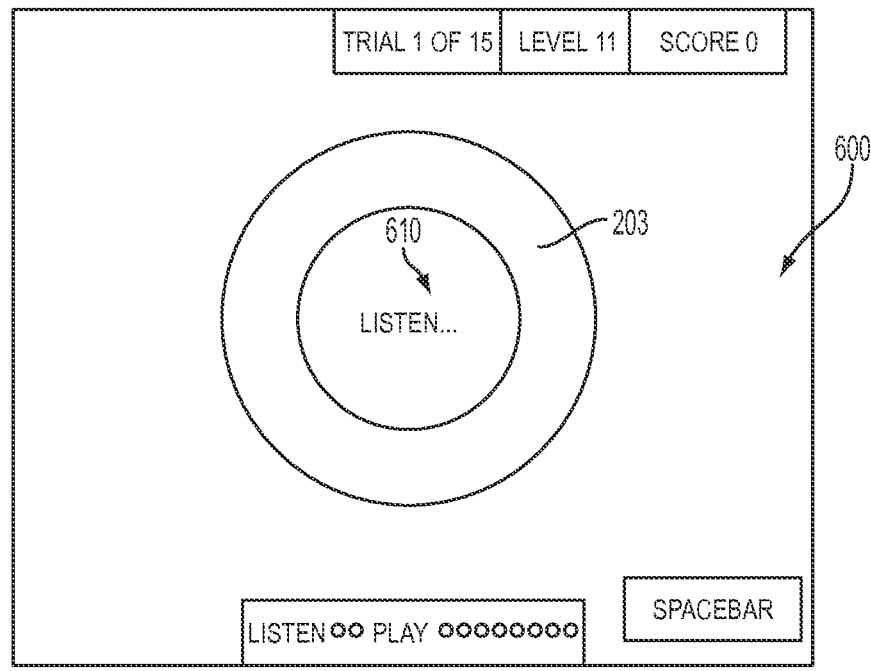
FIG. 6 shows a further game mode screen display according to aspects of the disclosed subject matter.

As can be seen in the views of FIGS. 1-4 lower levels of user cognitive skill training can feature constant visual cues, such as those noted in those figures. Lower trial numbers within a given level may also be configured in the same way, i.e., with visual and/or audio cures disappearing at a later trial level. As an example illustrated in FIGS. 4C and 5, the visual cues have disappeared at trial 4 of levels 5 and 10, respectively, with only, in some embodiments, the correct indicators 220, 220' or incorrect indicators 230 remaining. These indicators, 220, 220' and 230 may fade out as the rhythm timing continues around the rhythm track 203 to be available for later use in the continuing circumnavigation of the rhythm timing trial around the rhythm track 203. According to aspects of embodiments of the disclosed subject matter, as seen on the screen display 600 in FIG. 6, at some level and above, e.g., level 11, the rhythm timing markers disappear even from the first trial onward, and including the preparatory "LISTEN" mode 610.

Figure 7:
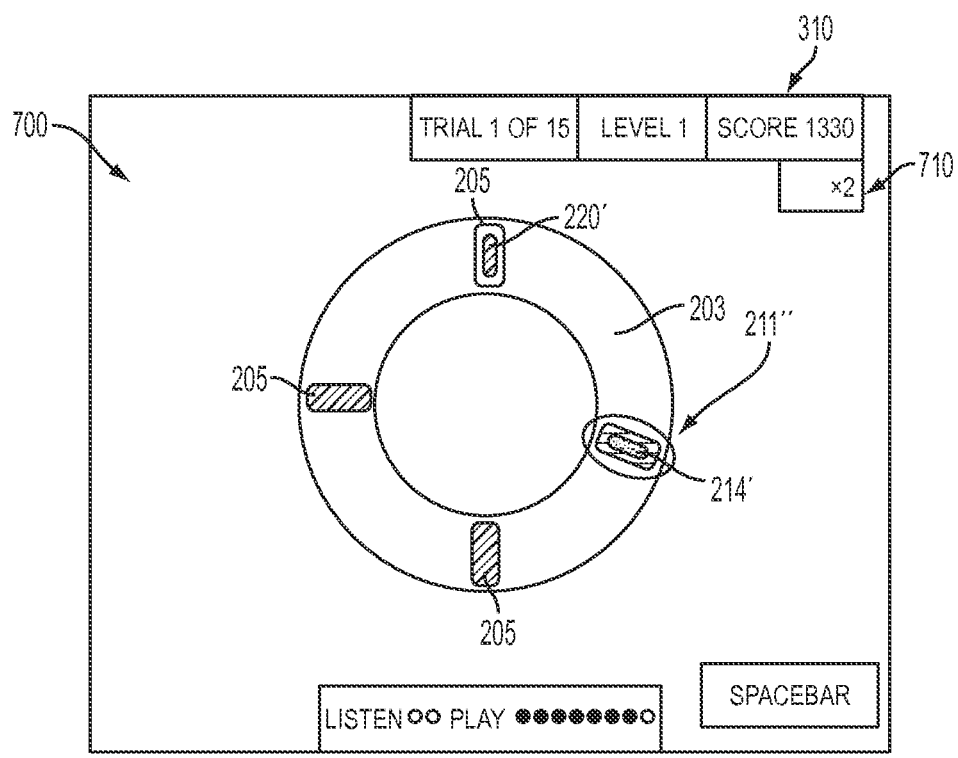
FIG. 7 shows a further game tutorial screen display according to aspects of the disclosed subject matter.

FIG. 7 illustrates a rhythm cognitive skill training game playing mode where, as an example, a score multiplier has been initiated by the user computing device, as indicated by the "x2" multiplier 710 shown in the screen display 700 of FIG. 7. This can, in some embodiments, be a new mode starting at a new level 1, as indicated in the mode information bar 310. In addition to the visuals display 710, distinct sounds, such as beeps, reminiscent of arcade video game sound effects may be generated whenever the score multiplier 710 is turned on or off, and/or when the score multiplier is in use. Such sounds can contrast with the rhythm's instrumental sounds and enhance the audio feedback effects, consistent with in other Lumosity® games. Other visual feedback may be employed such as the moving rhythm timing marker 211", when displayed, may be a different color, like orange, including a different shade for its sweet spot 214'.

The score multiplier 710 may also be activated by the user computing device due to user performance, for example, if the user has a score at or above some threshold, such as 100% accuracy, for some period of time, i.e., two rhythm cycles, which here is circumnavigation around the rhythm track twice. This could be indicated by the moving rhythm timing indicator making such circumnavigations or by sounds when the moving rhythm timing indicator is not being displayed. In the latter case, the visual indication could be the change in color of some other part of the display, such as the rhythm track turning orange. The multiplier could them be set to incrementally increase by some selected amount(s) for each additional cycle above the accuracy threshold, as an example.

Figure 8:
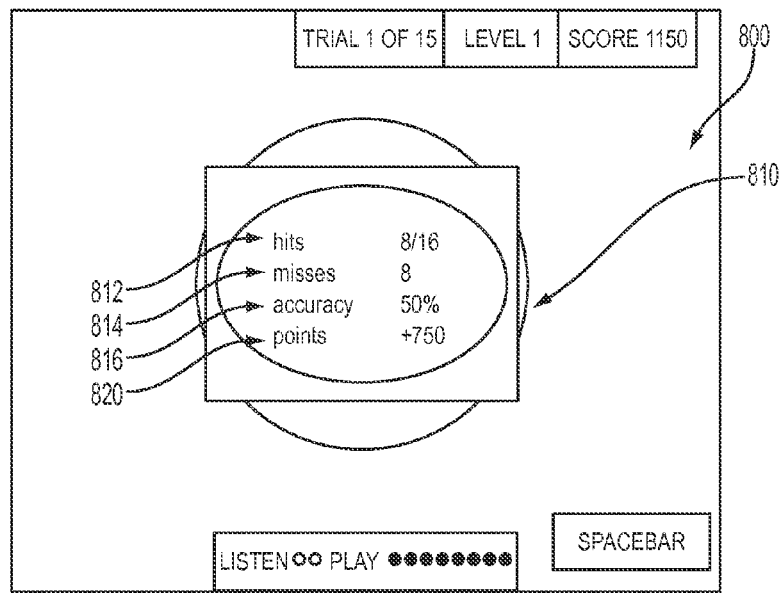
FIG. 8 shows is a game results screen display according to aspects of the disclosed subject matter.

FIG. 8 shows is a game results screen display 800 according to aspects of the disclosed subject matter. The game results screen display 800 can have a game information box 810, which can display a hits indication 812, a misses indication 814, and an accuracy percent indication 816. The game results screen display 800 can also display a points indicator 820.

According to aspects of embodiments of the disclosed subject matter, feedback may be provided to the user, for example, at the end of a trial. Also in the disclosed embodiments, a user may be automatically started at a level below where the user last finished the next time the user plays a new game. Also embodiments may have the user computing device randomly generate the rhythms for a trial, e.g., according to a set of rules that control the variables listed below. The user computing device may utilize a matrix that outlines how these variables can be specifically controlled for each level. In the game programming, rhythms may be represented as a series of 1's and 0's, where 1=hit and 0=rest. Levels, listed from an example of easy to an example of hard, may include a number of notes (i.e., a number of 1's according to number of the level of the game being played by the user). Another variable may be visual input cues, which may be represented by (00) always present, (01) gradually fade and (10) absent). Another variable may be tempo, which may be represented, e.g., by (00) medium tempo, (01) slower tempo and (10) faster tempo. Still another variable may be measures played, e.g., (01) one 4-beat measure and (10) two 4-beat measures). According to aspects of embodiments of the disclosed subject matter, a certain selected number of levels, e.g., levels 1-14 may be a single 4-beat measure and subsequent levels may be two four beat measures. In viewing the rhythm timing circle on the game user interface screen display, downbeats may be considered to correspond to the positions at each of the four cardinal compass point directions. Syncopated beats can then between these points. It will be understood that in levels that include two measures, double the number of beats lie on the rhythm timing track, so that beats lie twice as close to each other. Rhythm difficulty can also increase with level number by increasing the number of syncopated notes. According to an embodiment rhythm difficulty can be defined solely by the number of syncopated notes in a given trial, where syncopation refers to any note that does not lie on a downbeat.

It has been observed that non-musicians may start off paying more attention to visual cues than auditory cues. Although a goal of the game is to teach users to synchronize with external audio rhythms, without these initial visual cues, non-musicians may find the game overwhelming and frustrating. Thus according to one example of the rhythm based cognitive skill training game of the disclosed subject matter a leveling sequence may be utilized that can wean the user from the reliance on the visual cues and teach the user to listen more, by gradually removing visual cues after the user has had a chance to learn the rhythm for the given trial. Non-musicians may find the play of the game easier having their eyes closed, they may still need the presence of visual cues at first to gain an understanding about the game task (anticipation and duplication of the rhythm beats to be sounded), receive helpful feedback to train the users to listen better, and boost confidence in the performance by the user in order to successfully continue with game play.

Some players, such as younger players, may struggle to get to advanced levels because the idea of internalizing a rhythm does not seem to "click," even though they understand the user interface and try hard to tap the beats correctly. Users between their teens and thirties have been observed to outperform younger and older age groups. The user interface appears to be most intuitive to this age group.

Rhythm difficulty can be the least intuitive variable for which to control for in a rhythm-based cognitive skills training game leveling progression. One disclosed mode of leveling difficulty includes adding a number of syncopated notes in a given trial, where syncopation refers to any note that does not lie on a downbeat. This is one example of difficulty leveling and there may be others that more accurately track level progression. As an example, it has been found that syncopated notes that appear in a note group may be easier to play than isolated ones. For example, both the following 4-beat rhythms have two syncopated notes, but the first observed to be easier to play than the second, i.e., 11110000 and 01010000. It is believed that cleaner leveling algorithms can be developed by further investigating the available resources and qualitative observations. Some studies shown that musical rhythms can be quantitatively classified by level of difficulty. When developing this game's rhythm difficulty ranking system, as indicated in the Sadakata and Konguet-Higgins articles cited above, which present a framework for defining musical terms and awarding points based on these definitions to categorize rhythms based on the amount of syncopation and repetition within a musical phrase, however, limited testing with subjects with musical training and with content consisting of longer musical compositions in sheet music notation, and with more varied rhythms and complex thematic developments than the more isolated and consecutively repeated rhythms in the presently disclosed subject matter may result in the specific ranking systems developed in those studies not accurately reflecting difficulty of rhythms in the contest of the disclosed subject matter.

It has been found, however, that rhythms with equal lengths of rest groups may be easier for a user to follow and duplicate accurately than rhythms with different lengths of rest groups. For example, 10101010 and 10111011 are easier to follow and duplicate accurately than 1010010001 and 11010001, because the rhythm beats in the first two rhythm groups are consistently separated by one 0, i.e., for purposes of the present disclosure the equivalent in music of the continuation of a note for a second beat, i.e., a half note in a 4/4 measure, or the existence of a rest at the zero position. The second two rhythm beat groups in the second rhythm beat set are separated by a variable number of 0's. Rhythms with repeated rhythm beat groups are easier to play than rhythms with inconsistent rhythm beat groups. For example, 11011000 is easier than 10011000 because the first rhythm beat group repeats '11' twice and the second rhythm beat group has no repeated '1' groupings.

It will also be understood that syncopated rhythm beats are easier when they follow downbeat rhythm beats, rather than precede them. For example, both of the following rhythms contain a downbeat rhythm beat and a syncopated note, but 11000000 is easier to follow and duplicate accurately than 10000001, because the leading '1' followed by another "1" in the first example falls on one of the four cardinal direction points of the 4-beat rhythm circle.

According to aspects of embodiments of the disclosed subject matter, level-difficulty progression can be utilized to challenge the user enough to engage the user and help the user improve rhythm-based cognitive skills, but not challenge the user so much that the user can become overwhelmed and stop training. The level of fun and enjoyment of playing the cognitive rhythm-based cognitive skill training game at lower levels can be utilized to engage the user, even if the musical skills of the particular user are advanced enough to make the lower level difficulty levels still of interest. Eventually the user can reach a level after the beginning levels with an appropriate level of challenge without getting bored. Specific leveling increases such as regarding the removal of visual input cues, the increase in rhythm trial measure length or speed of occurrence of rhythm beats or the like can pose significant obstacles to a user. It will be understood that more gradual changes could be incorporated to help the user who struggles to make it past such transition points.

The fading and then absence of visual input cues could alternatively be made to fade out more gradually. As another example, the visual input cues could fade-in again, for example if the user score drops below a certain accuracy percentage (such as <40%) during a given rhythm trial at a level where fade out is occurring or has occurred.

It will be understood that other aspects of the rhythm-based cognitive skill training game can be increased in difficulty as levels increase, or with later trials at a given level, such as an increase in rhythm trial measure length. Measure lengths could increase gradually, and in addition rhythm difficulty could be reset to a slightly easier setting. It has been observed that a user may beneficially take advantage of certain techniques for properly playing the rhythm-based cognitive skill training game and advancing through the various levels and concomitant difficulty increases. As examples, the user may close his or her eyes and concentrate on listening; start hitting the spacebar during the "Listen" mode to get a head start; tap one's feet to the beat also; take turns switching between one's left and right hand for an enjoyable twist to the game; if one is off the beat, pausing to listen and internalize the rhythm before tapping the spacebar again and finally, utilizing the feedback from the game, such as the location of the red lines that shows whether the incorrect response input is late or early on a given beat so that the user can adjust.

It will further be understood that the rhythm-based cognitive skill training game may include any number of other features to make the game more fun and engaging. As one example, the length of each trial level could be lengthened, such that the user can more fully become involved with the rhythm being followed and duplicated—to "get into it" so to speak. Increasing the amount of "Listen" loops could also be beneficial to user comfort. At the same time, the training game needs to maintain some level of fast-paced dynamic increases frustration, even if the game becomes a bit less musical, however, maintaining the challenging environment can be very beneficial for the intended cognitive skill training. The above noted "tips" can be communicated to the user, e.g., through the display screen or audio signal or both.

In addition to color coded feedback, for example, blue=correct and red=incorrect, other information could be displayed such as the points scored for each correct rhythm timing input by the user. The feedback can be balanced with any effects of detracting from the musicality of the game, such as the effect of distracting the user from internalizing rhythms the user may feel that such additional feedback during game play inhibits the user from focusing on the rhythm and having an uninterrupted streak of correct responses.

In addition to a score multiplier as a "reward" for sustained correct inputs, the game may generate or otherwise utilize other "rewards." Such rewards could be visual and/or audio. Examples of an audio multiplier reward could be increasing the volume or adding a melody to the notes. Examples of a visual multiplier reward could be adding images of fans in a crowd or fireworks. Utilizing a glowing multiplier marker and an audio signal announcing the multiplier is in effect can be a more subtle announcement and accomplish the same goal of rewarding and motivating the user to strive for repeated successful gameplay. As another example, because it is often the case that a user may repeatedly miss the same note on a rhythm loop within a given trial, as an aid to identifying such mistake and improving the results for the user, the game could show the individual accuracy scores for each beat or point out the beat(s) where the user has performed at the lowest accuracy percentage. The game could also notify a user of common general mistakes being make, such as coming in late/early, missing the first note in a group of notes, or missing syncopated notes.

According to aspects of embodiments of the disclosed subject matter certain aspects of the proposed rhythm-based cognitive skill training game can make the game have a more recognizable relation to everyday encounters with music. While a trained musician or vocalist may easily see the value of the proposed rhythm-based cognitive skills training game, non-musicians/vocalists may struggle to make this connection. It is believed that emphasizing the importance to rhythm to musicality will not only make for a game that can more successfully train cognitive skills relating to skills in recognizing and duplication the associated rhythm, but also make the game more fun. As an example, allowing the user to make external sounds, such as may be used for input through the use of a microphone for the user could make the game more fun and relevant to music, as opposed to simply pressing a keyboard key. Clapping hands or tapping drumsticks on a hard surface, as examples, are two other alternative means of user input.

Figures 9A, 9B:
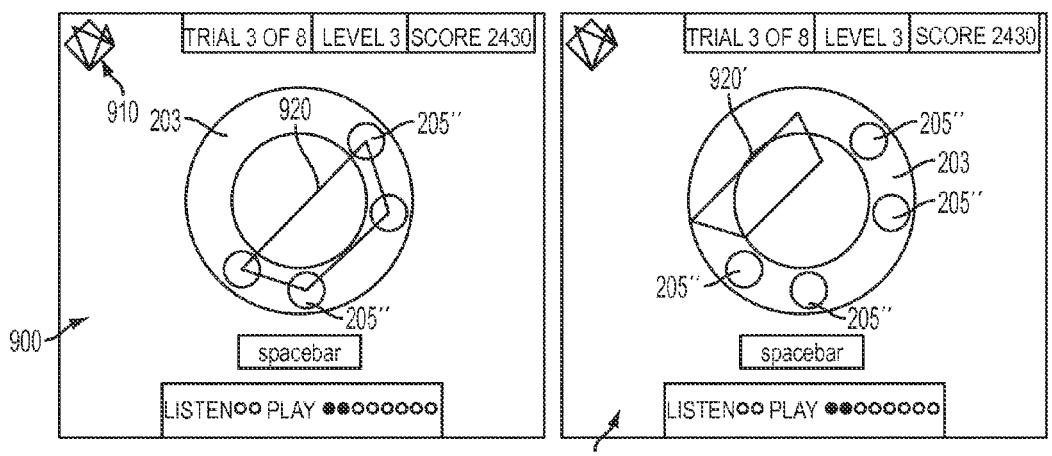
FIGS. 9A and 9B show a game mechanics screen display according to aspects of the disclosed subject matter.

According to aspects of embodiments of the disclosed subject matter audio layering can be utilized including playing background rhythms along with the current rhythm the user is trying follow and duplicate. Such audio layering could actually be utilized to either decrease or increase the difficulty of a trial, depending on the complexity of the background rhythm and whether or not it complements the trial rhythm the user is currently attempting to follow and duplicate. According to aspects of an embodiment as illustrated by way of example in FIGS. 9A and 9B, which show game mechanics screen displays 900 and 900', a rhythm reward token 910 could be generated and displayed on the screen display 900, 900'. The rhythm reward token 910 could start as a rhythm polygon 920, as illustrated in FIG. 9A. The rhythm polygon 920 can connect all of the stationary rhythm timing markers 205' in FIGS. 9A and 9B from within a given rhythm timing track 203, and, for example, appear if a user attained some threshold level of accuracy such as 80% correct for the trials using such rhythm timing. This polygon could then become a reward token 920', and be moved off to the side of the screen display 900', as shown in FIG. 9B and become part of the rhythm reward token 910 (though not shown in the figures with the reward token 920' included). The audio delivery of the rhythm represented by the rhythm polygon 920' as it leaves the trace 203 containing the stationary rhythm timing markers 205' for a new trial to begin with different timing markers 205', can continue in the background at a lower volume as the next rhythm trial appears. The complexity of the background rhythm could be controlled by the number of previous rhythms that remained playing.

Figure 10A:
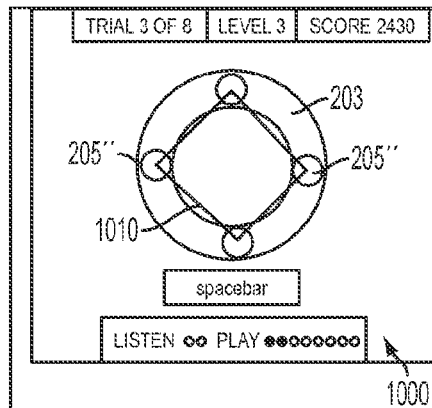
FIGS. 10A-C show further game mechanics screen displays according to aspects of the disclosed subject matter.
Figure 10B:
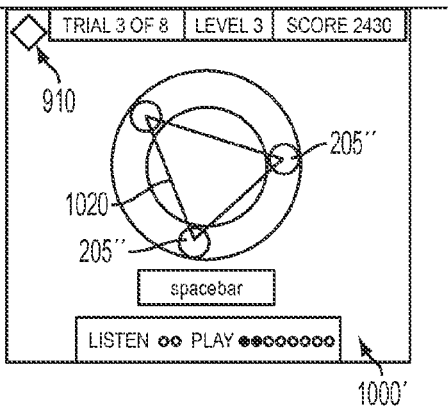
Figure 10C:
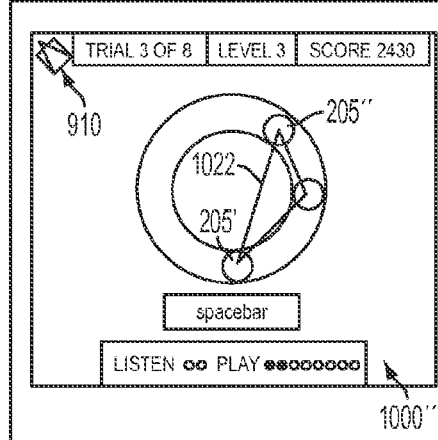

An overall representation of the layered background rhythms in the stacked reward token 910 can be constructed as follows. As an example, first a diamond shaped rhythm pattern 1010, as seen in the screen display 1000 of FIG. 10A can be formed, and when the user achieves a greater than 80% accuracy rate, this diamond shaped rhythm reward token can be moved, as illustrated in FIG. 9, over to form a first part of the reward token 910, as seen in FIG. 10B. Another shape can be added, as shown in FIG. 10C, to form a stacked polygon theme, i.e., using the triangular shape of the rhythm polygon 1020 from FIG. 10B after the user achieves the requisite accuracy percentage, to form the reward token 910 shown in FIG. 10C. The background rhythm can then include the complex beat rhythm of the combination of the rhythm represented by the diamond 1010 and the triangle 1020, to which may then be added the triangle rhythm beat polygon 1022 to form the reward token 910 as seen in FIGS. 9A and 9B, and have its own rhythm beat pattern added to the background rhythm.

Figure 11A:
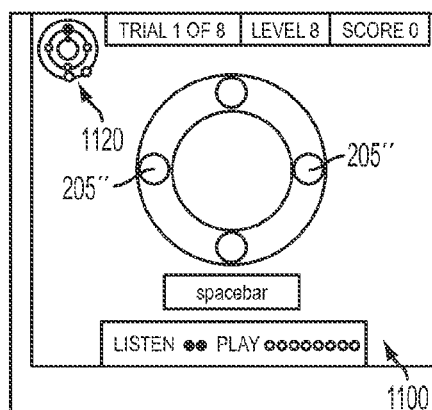
FIGS. 11A-B show further game mechanics screen displays according to aspects of the disclosed subject matter.
Figure 11B:
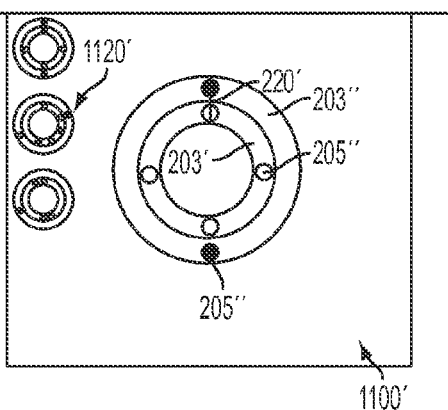
Figure 12:
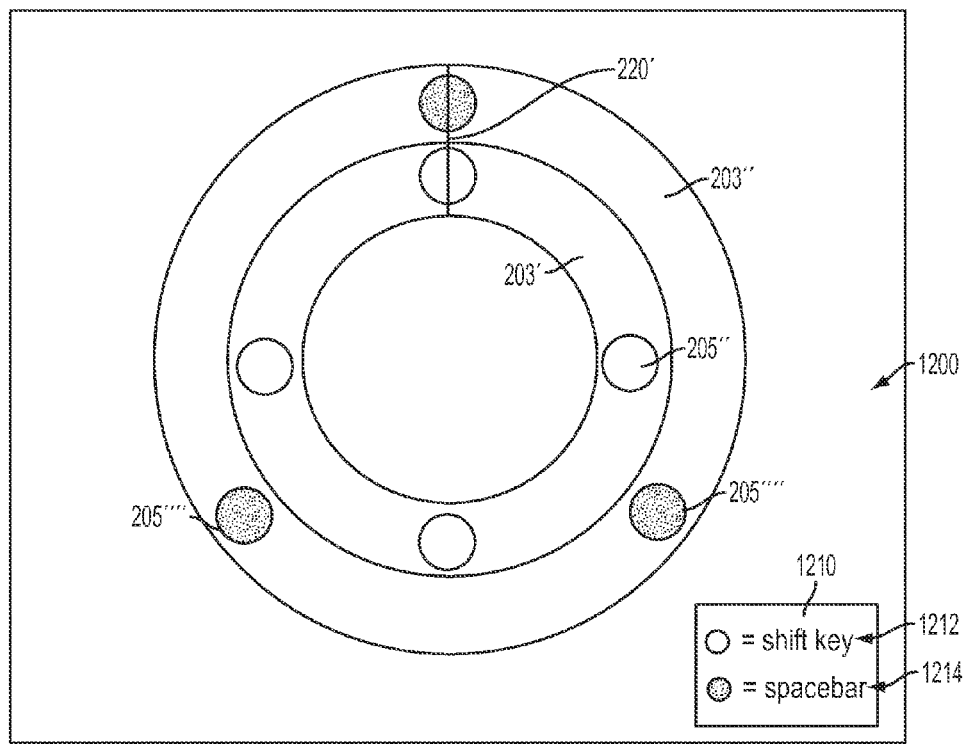
FIG. 12 shows a further game mechanics screen display according to aspects of the disclosed subject matter.

According to aspects of an embodiment of the disclosed subject matter, a similar reward token 1120, as seen in FIG. 11A could be constructed using concentric circles, each representing a rhythm beat pattern as illustrated by the respective stationary rhythm beat markers on respective rhythm timing tracks, starting with the inner track as a first reward token and with successive tracks added to form the reward token 1120, as illustrated in FIG. 11A. Similarly, as represented in FIG. 11B a two handed rhythm beating timing tracking aspect of the rhythm-based cognitive skill training game could represent a rhythm timing track 203' for the right hand of the user, with stationary rhythm timing markers 205', and a rhythm timing track 203" for the left hand of the user, with stationary rhythm timing markers 205". The two handed rhythm track in the screen display 1100' can utilize a moving rhythm timing bar 220, which the user can utilize to time the input of the user for each hand according to when the moving bar passes over one or both of the stationary rhythm timing markers 205' and or 205" as it circumnavigates the tracks 203', 203". In this event, the reward tokens 1120', instead of being stacked, may be shown as separate prior rhythm, again with possible audio of one or more playing in the background as the user works on the next rhythm timing pattern. It will be understood that for two handed rhythm beat tracking and duplication, according to an embodiment of the disclosed subject matter, the two handed input, as illustrated by way of example in FIG. 12, may be accomplished using different input elements for each hand, e.g., the shift key for the lighter stationary rhythm input markers 205''' on the inner track 203' and the spacebar for the darker stationary rhythm input markers 205''' on the track 203", which a respective one is crossed by the moving rhythm timing marker bar 220'.

An additional level of challenge may be implemented by the computing device, such as a rapid-fire challenge round. Such a rapid fire challenge round could present to the user, for example, a series of rhythms to master (~5) by providing the typical two "Listen" loops but then only providing 2 "Play" loops before moving on. To increase the intensity of this feature, the transitions with accuracy percentage and score could be omitted, in lieu of real time points appearing on screen next to accurately played beats. The score of the user could then be displayed at the end of the rapid fire challenge round.

A number of possible enhancements to increase user interest and satisfaction could be included which could also add credibility to and build excitement around the rhythm-based cognitive skills training game's education value. For example, an image of the sheet music notation for a rhythm that a user has just mastered could be displayed at the end of a given trial. Alternatively, a booklet of mastered rhythms could be created by the computing device and appear after gameplay and the user given access to the book. Transitions between trials or levels could be utilized also to teach users about basic music vocabulary, such as tempo, time signature, syncopation, timbre, and quarter, eighth, sixteenth, and triplet notes. Dance rhythms fitting with international styles like rumba, waltz, tango, swing, cha cha and polka could characterize each level to help players recognize them in the future. Highlights of popular songs that fit with the time signature and rhythms a user has just mastered can be provided, which can enable the user to look them up separately and clap along.

An added level of complexity could be provided by having the user mimic the tempo and the length of a note, e.g., one lasting for more than one beat in a given measure. As an example, a user could be required to hold down or remain in contact with the touch screen virtual representation of the spacebar for the indicated duration of a note, rather than just tap the spacebar. This feature parallels the variety of note lengths found in sheet music for most instruments.

Other themed concepts initially explored include fishing, as illustrated in FIG. 17D, knocking secret passwords on a door, as illustrated in the screen display 1610 of FIG. 16B, cracking Morse code puzzles, as illustrated in the screen display 1600 of FIG. 16A and water ripples, as illustrated in the screen display 1730 of FIG. 17C. Possible screen displays of these contemplated embodiments are depicted, as examples, in FIGS. 16A-16D and 17A-17F. A fishing reel rhythm is illustrated in FIG. 17D and a typewriter rhythm is illustrated in FIG. 17E, as well as a cannon shot scoring illustration in FIG. 17F. Informational screen displays 1620 and 1650 are illustrated in FIGS. 16B and 16C.

According to aspects of embodiments of the disclosed subject matter the rhythm-based cognitive skills training game can have a variety of graphical user interfaces ("GUIs"). Circular visual input, warning and may be utilized as shown in the FIGS., e.g. in the screen displays 900 and 900' of FIGS. 9A and 9B, the screen displays 1000, 1000' and 1000" of FIGS. 10A-10C, in the screen displays 1100 and 1100' of FIGS. 11A and 11B, in the screen display 1200 of FIG. 12 in the screen displays 1300, 1300', 1300", 1300''', 1300'''' and 1300' of FIGS. 13A-13F, in the screen displays 1400, 1400' and 1400" of FIGS. 14A-C, in the screen display 1650 of FIG. 16D and in the screen displays 1700 and 1710 of FIGS. 17A and 17B. However, ovals or ovoids may provide more precise information and, thus have been found to be positively received among users. Such are illustrated by way of example in the screen displays 201 of FIG. 2, 300, 300', 300" and 300''' of FIGS. 3A-3D, 400 and 400' of FIGS. 4A and 4B, the screen display 500 of FIG. 5 and the screen display 700 of FIG. 7. The moving rhythm timing indicator may be in the form of a rod as shown at 220' in the screen display 1200 of FIG. 12 or 1440 as shown in the screen display 1400''' in FIG. 14E, or as a rotating radius such as is shown at 1452 in the screen display 1400' of FIG. 14F, which can provide for even more precision in measuring the concurrence of the user input with the respective moving crossing the respective stationary marker, if that is an objective, and even applies to granting partial scores for partial concurrence. As an example, the computing device may be configured to only score a correct input if the concurrence and the input are within some threshold, e.g., 200 ms, or variable scores for differing time ranges, e.g., 50% for within 250 ms and 25% for within 300 ms.

Figures 13A, 13B:
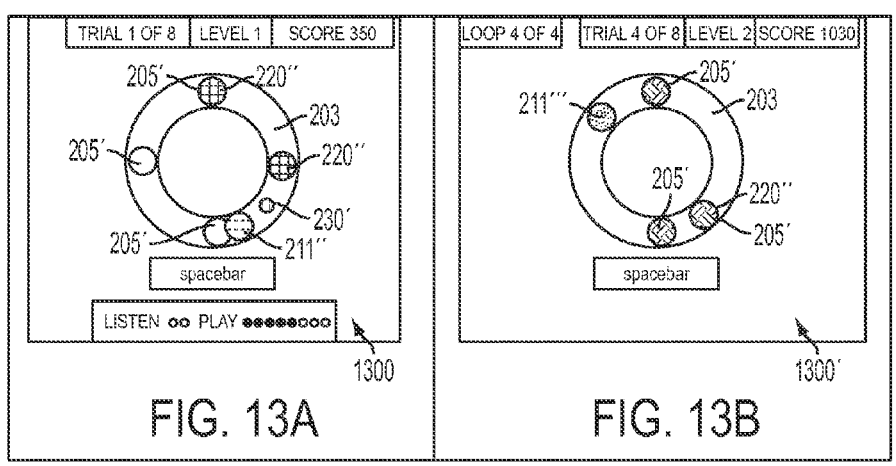
FIGS. 13A-F show further game mechanics screen displays according to aspects of the disclosed subject matter.
Figure 13C:
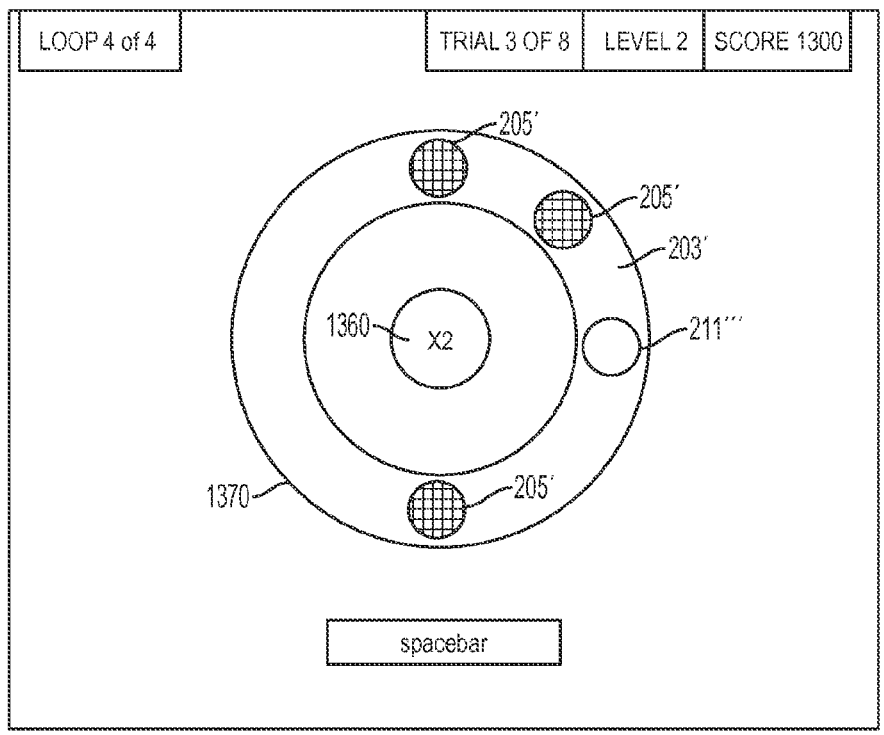
Figure 13D:
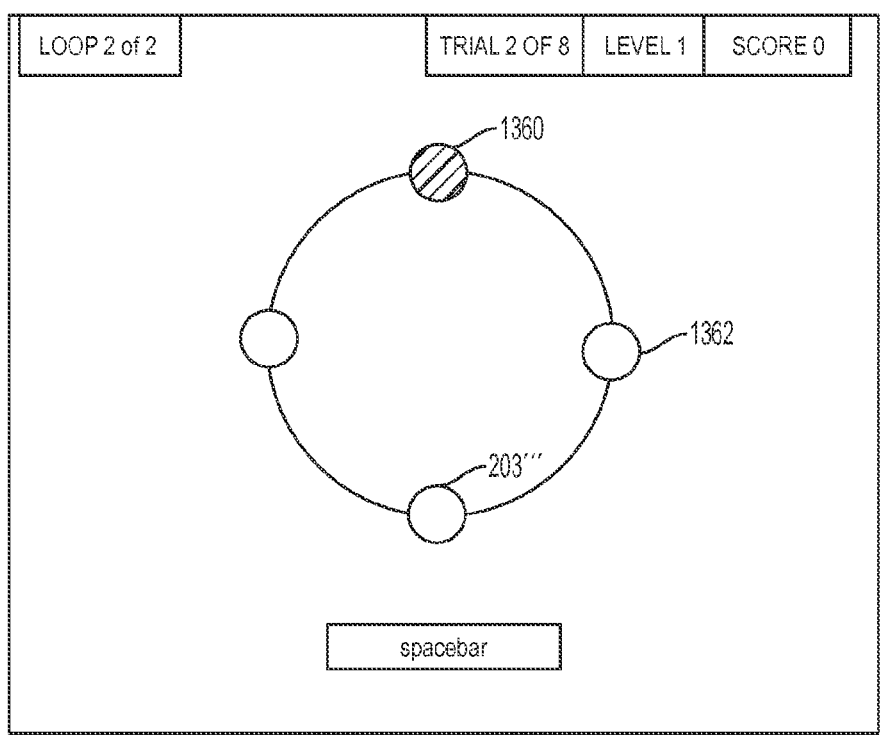
Figure 13E:
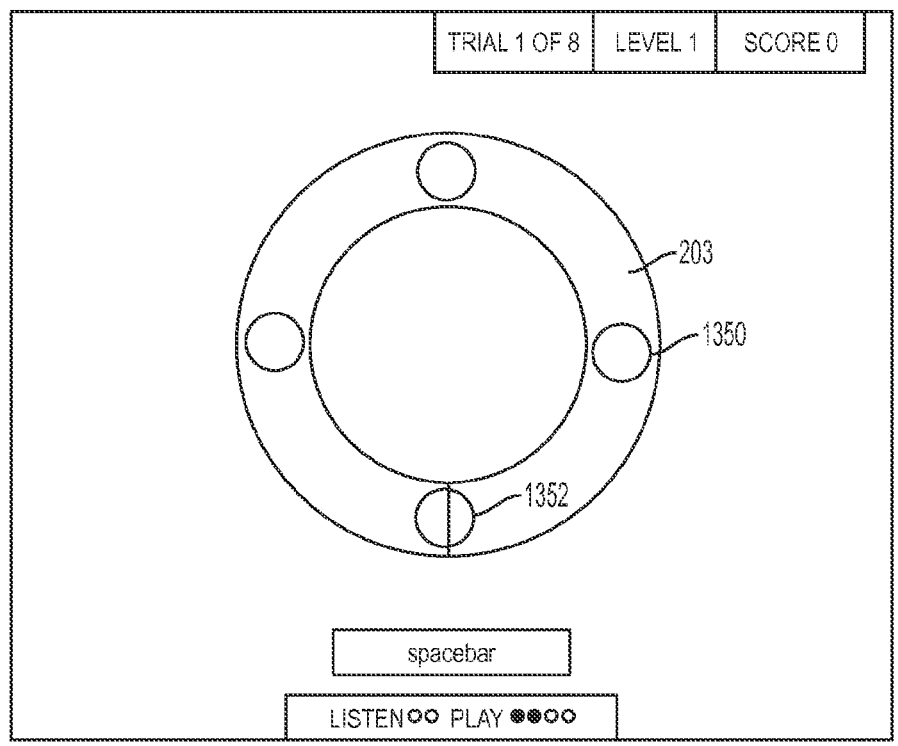
Figure 13F:
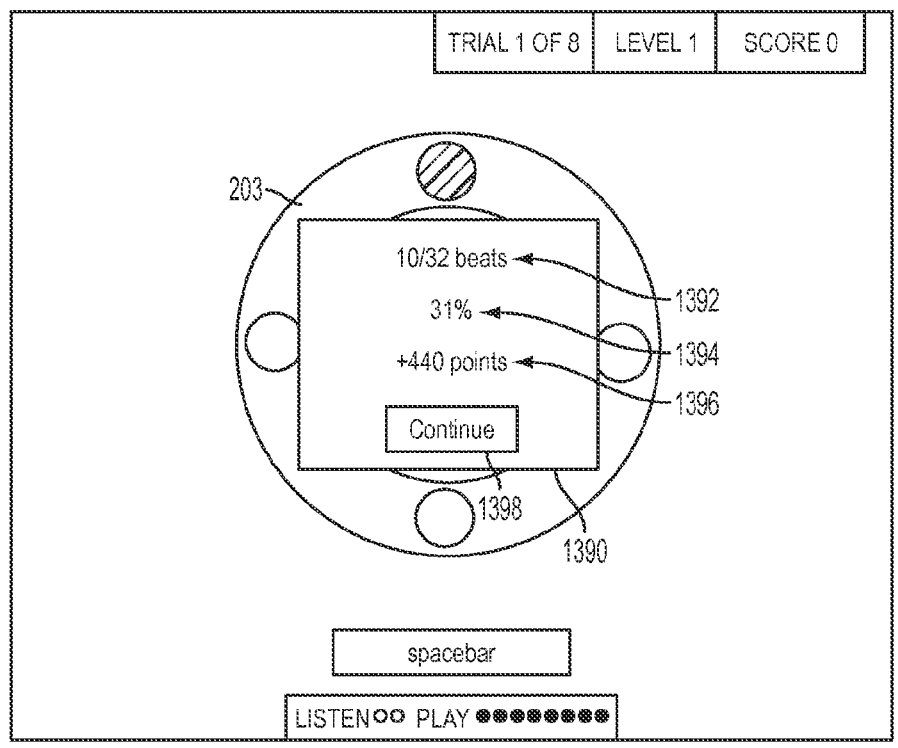

A possibility for the screen display representation of the game mechanics for a rhythm-based cognitive skill training game could include a white, glowing halo 1370 as illustrated in the screen display 1300" of FIG. 13C, in place around the rhythm timing track 203 and the multiplier number 1360 in the center of the rhythm timing track 203 circle, as illustrated in FIG. 13C. FIGS. 13A-F are illustrative of several variations of the screen displays 1300, 1300', 1300", 1300''', 1300'''', and 1300''''', having rhythm timing tracks 203, stationary rhythm timing markers 205', a white moving rhythm timing marker 211' (in FIG. 13B) and a dark moving rhythm timing marker 211" (in FIG. 13A). Also shown in FIG. 13B is a possible correct perception input indicator 220", comprising a green halo around the center of the stationary rhythm timing marker 205'. An incorrect input marker 230' is shown in FIG. 13A. A circular rhythm rail track 203' is illustrated in FIG. 13C, having stationary rhythm timing markers 1362 and a larger diameter moving rhythm timing marker 1360 traveling around the rail ring 203'''. FIG. 13E illustrates white circular stationary rhythm timing markers 211''' on a circular rhythm timing track 203 with a moving rhythm timing marker bar 1352, which may, e.g., need to align with the center of the particular circle 1350 for a correct input. FIG. 13F illustrates a rhythm timing track 203 having displayed over the top of it an information box 1390, which may contain a total beat count and number of correct inputs 1392, a percentage accuracy 1394, a number of points 1396 and a continue button 1398.

The alternative of shifting to the oval time marker transforming from white to the orange marker 214', as discussed above in regard to the screen display 700 of FIG. 7, and the multiplier number being moved to the upper right-hand corner of the screen display 700 of FIG. 7, would appear to be at most, very subtle differences in the GUI of the game. Some users may find the first location more interesting and some may prefer the latter, finding the former interferes with concentration on the tracking and duplicating the rhythm pattern during game play.

Figure 14A:
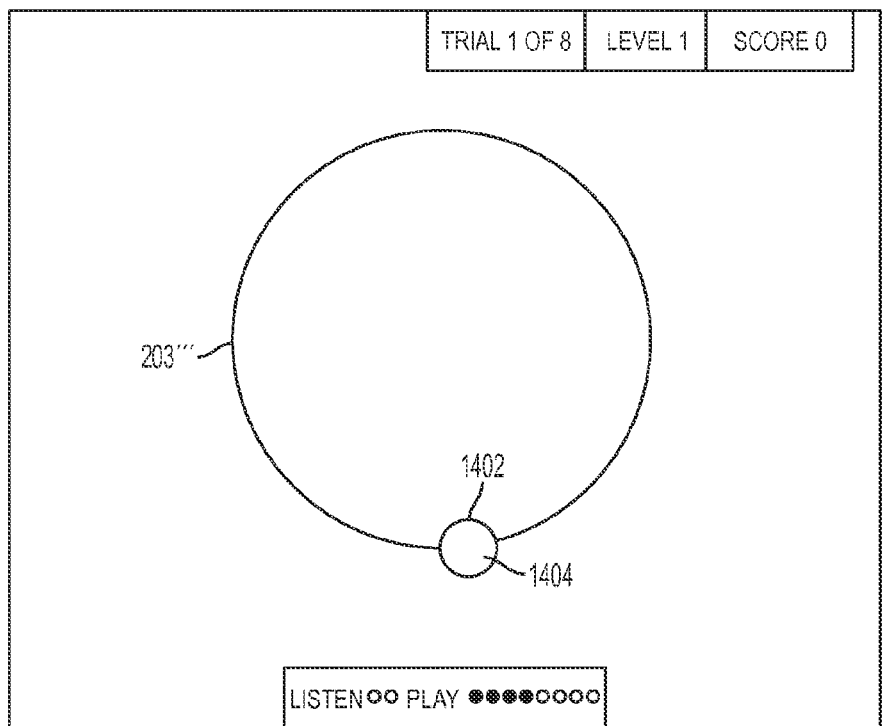
FIGS. 14A-I show a further game mechanics screen displays according to aspects of the disclosed subject matter.
Figure 14B:
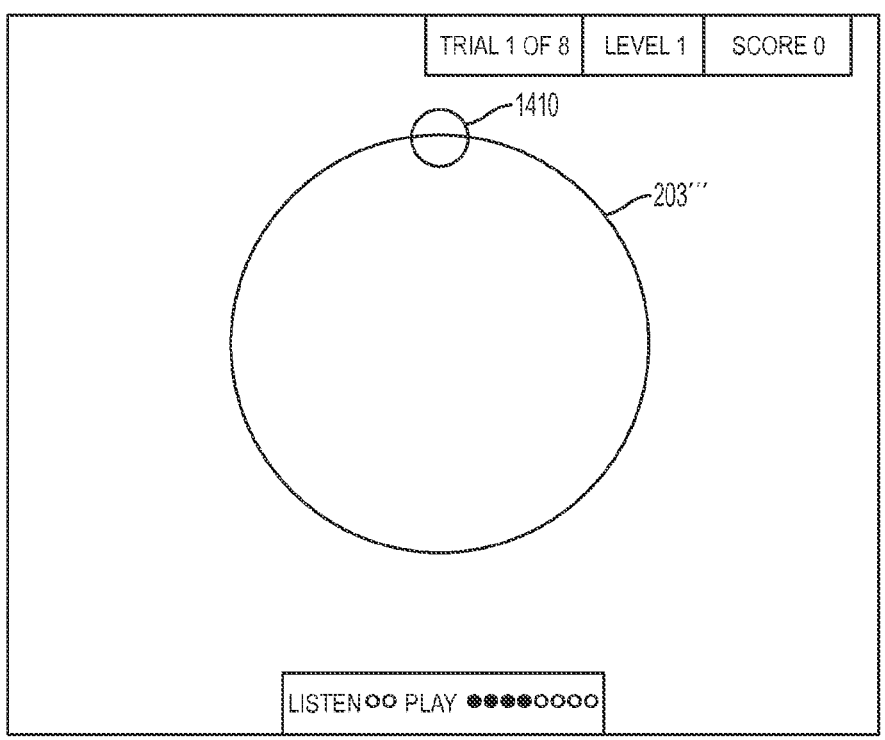
Figure 14C:
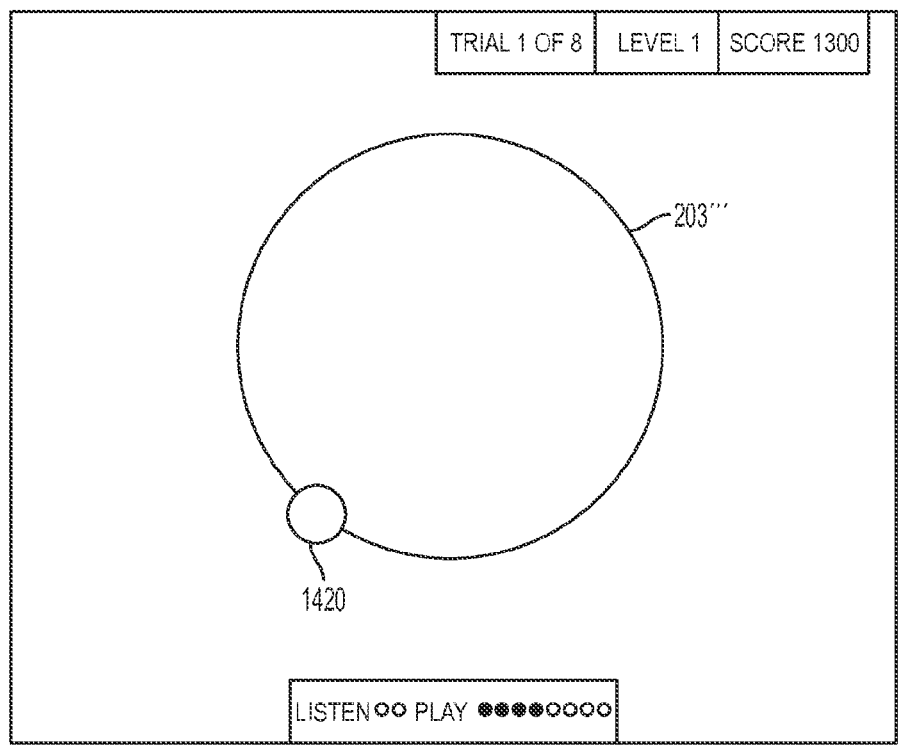
Figure 14D:
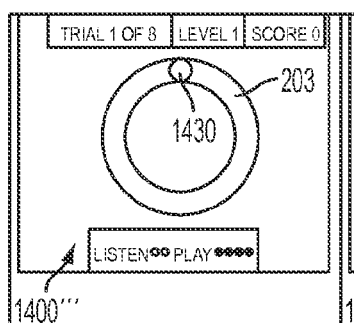
Figure 14E:
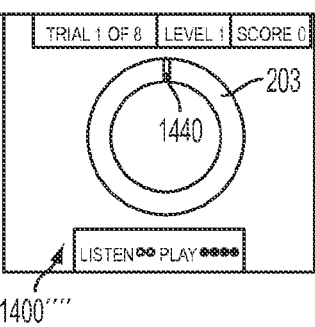
Figure 14F:
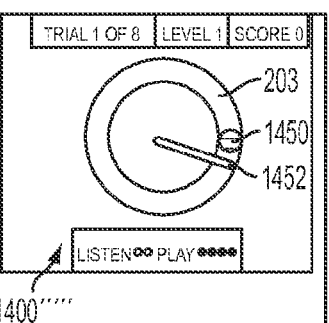
Figure 14G:
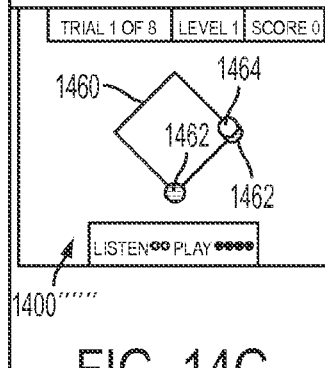
Figure 14H:
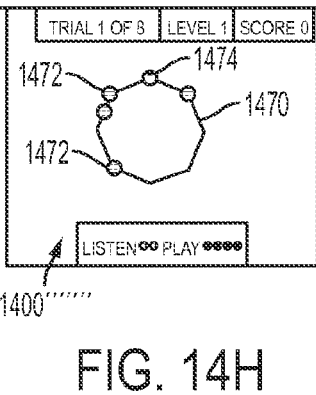
Figure 14I:
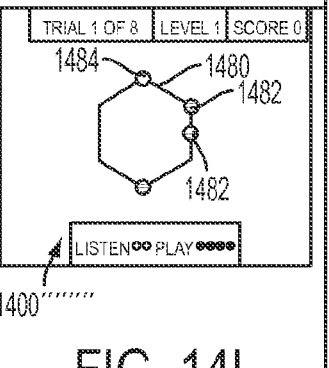

FIGS. 14A-I illustrate additional possible variations of a rhythm-based cognitive skills testing apparatus and method according to aspects of embodiments of the disclosed subject matter, e.g., having a rhythm track ring rail 203''' (in the respective screen displays 1400, 1400', 1400" of FIGS. 14A-C), a circular rhythm timing track 203 (in the respective screen displays 1400''',1400'''' and 1400''''' of FIGS. 14D-F) and polygonal rail rhythm timing tracks 1460, 1470 and 1480 (in the respective screen displays 1400'''''', 1400''''''' and 1400'''''''' of FIGS. 14G-I).

In FIGS. 14A-C, there is shown, as examples, a stationary rhythm timing marker 1402 with a smaller moving rhythm timing marker 1404, a moving rhythm timing marker ring 1410 with no stationary timing markers visible and a solid moving rhythm timing marker 1420 with no stationary rhythm timing markers visible. In FIGS. 14D-F there is illustrated, as examples, a solid moving rhythm timing marker 1430, a moving bar rhythm timing marker 1450 and a moving rhythm timing radius 1452 and a stationary rhythm timing marker 1450. FIGS. 14G-I illustrate, as examples, a diamond polygon rail rhythm timing track 1460, with stationary rhythm timing markers 1462 and a moving rhythm timing marker 1464 (in FIG. 14G), an octagonal rhythm timing track 1470, with stationary rhythm timing markers 1472 and a moving rhythm timing marker 1474 (in FIG. 14H) and a hexagonal rhythm timing track 1480, with stationary rhythm timing markers 1482 and a moving rhythm timing marker 1484, in FIG. 14I.

According to aspects of embodiments of the disclosed subject matter, it may be advantageous to provide, a game introduction sequence that is capable of smoothly transitioning between rhythm tracking and duplication trials and, also, intuitively cue the user about when to listen and when to play. Introduction sequences from some of the games mentioned above were examined and at least initially the game of the present application was configured to have two cycles to listen to the rhythm and two cycles to play along. However, it was found that having a longer play cycle (e.g., increasing to eight, for a given trial) reduced confusion as to when to be listening and when to be playing. However, these numbers could vary—the number of either the Listen and Play cycles could be kept as is or increased, depending on what user reaction is intended to be invoked and/or tested. The "Listen", "Play" bar 320 can serve to assist the user in following how far along the user is in a given rhythm trial. Such a bar may be unnecessary, as some users may not even pay attention to this display during game play. Given this subtlety a larger, bolder text display may be introduced in the center of the rhythm timing track circle, as illustrated at 610 in FIG. 6. This caught user's attention much more successfully. Other possibilities include, for example, displaying in text form "1,2,3,4 . . . Play," and "Listen, Play." Alternatively four clave beats (with no text) could be introduced, followed by the rhythm trial playing accompanied by the text "Listen, Ready?, Play!" as the moving rhythm timing marker circumnavigates the track being displayed. It may prove necessary that users be cued to "Play!" in anticipation of when actual scoring begins, lest they be penalized for coming in late.

According to aspects of embodiments of the disclosed subject matter, audio feedback for the user may be reduced or eliminated entirely. The sound representing the correct playing of the rhythm trial with which the user is being prompted to synchronize and duplicate could be eliminated, for example. Users may find other ways to synchronize by, for example, simply closing their eyes while listening in order better concentrate on the audio for a period of time. However, in doing so a user could lose real-time feedback on the performance of the user, if only based on visual indicators, such as appearance of correct and incorrect markers in different colors. Adding an audio feedback component corrects this possible shortcoming. The user can then hear when the user is off-beat. While this incorrect audio feedback could be the same instrumental sound as the correct rhythm trial playing in the background, such a similarity could also confuse and fluster the user who does not separate the correct rhythm trial playing in the background and the incorrect input audio feedback. A mitigation could be to reduce the volume of the negative audio feedback for example, from 0.2-0.4 of the volume of the correct rhythm trial. Another approach is to use a completely different audio incorrect signal, which might also then remain constant throughout the game play. For the same reasons, according to aspects of embodiments of the disclosed subject matter, other unique audio feedback sounds may be utilized and such sounds may be chosen to avoid overlap with the rhythm's instrumental sounds.

In addition, according to aspects of embodiments of the disclosed subject matter various instrumental sound types may be utilized make the rhythm-based cognitive skills training game more interesting and seem more musical. Such sounds could mimic, e.g., the sound(s) of a bongo drum(s), a shaker, a conga, a snare drum, a hand-drum, a tambourine and a cowbell. Choosing sound can be important in order not to produce sound that is too diffuse, thereby possibly causing the user to focus attention on whether to press the spacebar towards the start or end of the sound. Sounds can, therefore be selected to have some variation, but also to be crisp and clear enough for the user to synchronize with the sound.

The disclosed subject matter is described in the present application with reference to one or more specific exemplary embodiments thereof. Such embodiments are provided by way of example only. It will be evident that various modifications may be made to the disclosed subject matter without departing from the broader spirit and scope of the disclosed subject matter as set forth in the appended claims. The specification and drawings are, accordingly, to be regarded in an illustrative sense for explanation of aspects of the disclosed subject matter rather than a restrictive or limiting sense. Numerous variations, changes, and substitutions will now occur to those skilled in the art without departing from the disclosed subject matter. It should be understood that various alternatives to the embodiments of the disclosed subject matter described as part of the disclosed subject matter may be employed in practicing the disclosed subject matter. It is intended that the following claims define the scope of the disclosed subject matter and that methods and structures within the scope of these claims and their equivalents be covered by the following claims.

What is claimed is:

1. A method of training a cognitive skill comprising:
providing, via a user computing device user interface display, musical rhythm training comprising at least one trial comprising:
displaying on the user interface display, via the user computing device, a rhythm track comprising at least one stationary beat timing mark and at least one moving beat timing mark repeatedly moving along the rhythm track;
receiving via a user interface input an indication from the user that the user perceives a moving beat timing mark to be coincident with a stationary beat timing mark; and
providing, via the user interface, an indicator that the user is correct or not correct.

2. The method of claim 1, further comprising:
the rhythm track comprising a circle.

3. The method of claim 1 further comprising:
the rhythm track comprising a polygon.

4. The method of claim 3 further comprising:
the polygon comprising an equilateral polygon.

5. The method of claim 1 further comprising:
the stationary beat timing mark and the moving beat timing mark are distinguishable from each other by at least one of composition and color.

6. The method of claim 1 further comprising:
the rhythm track comprising a plurality of rhythm tracks, each comprising at least one stationary beat timing mark and at least one moving beat timing mark repeatedly moving along the respective rhythm track at a respective uniform speed.

7. The method of claim 1 further comprising:
providing a correct rhythm beat timing indicator on a respective stationary beat timing mark when user the perception indication is coincident with the stationary beat timing mark.

8. The method of claim 7 further comprising:
the plurality of rhythm tracks comprising a left hand rhythm track and a right hand rhythm track; and
providing a correct rhythm beat timing indicator on a respective stationary beat timing mark when the user perception indication is coincident with the stationary beat timing mark on one of the respective right hand rhythm track and left hand rhythm track.

9. The method of claim 1 further comprising:
eliminating, via the user computing device, the moving beat timing mark;
receiving, via the user interface input, a perception indication from the user that the user perceives a beat timing being coincident with a stationary beat timing mark to occur.

10. The method of claim 1 further comprising:
determining, via the user computing device, that the performance of the user has reached a preselected accuracy threshold;
displaying, via the user interface display, for the next and subsequent trials a visual indicator that the user scoring has been advanced by a selected multiple.

11. The method of claim 10 further comprising:
including, via the user computing device, an audio indication that the user scoring has been advanced by the selected multiple.

12. The method of claim 11 wherein the preselected accuracy threshold comprises a threshold accuracy level maintained by the user over a selected period of time.

13. The method of claim 12 further comprising:
maintaining, via the user computing device, the scoring being advanced by the selected multiple while the user continues to achieve the accuracy threshold.

14. A rhythm-based cognitive skill training apparatus comprising:
a user computing device configured to:
provide musical rhythm training comprising at least one trial comprising:
displaying on a user interface display a rhythm track comprising at least one stationary beat timing mark and at least one moving beat timing mark repeatably moving along the rhythm track at a uniform speed;
receiving via a user interface input a perception indication from the user that the user perceives a moving beat timing mark to be coincident with a stationary beat timing mark; and
providing, via the user interface, an indicator that the perception indication of the user is correct or not correct.

15. The apparatus of claim 14, further comprising:
the rhythm track comprising a circle.

16. The apparatus of claim 14 further comprising:
the rhythm track comprising an polygon.

17. The apparatus of claim 14 further comprising:
the polygon comprising a equilateral polygon.

18. The apparatus of claim 14 further comprising:
the stationary beat timing mark and the moving beat timing mark are distinguishable from each other by at least one of composition and color.

19. The apparatus of claim 14 further comprising:
the indicator that the perception indication of the user is correct is distinguishable from the indicator that the perception indication of the user is incorrect by color.

20. The apparatus of claim 14 further comprising:
the rhythm track comprising a plurality of rhythm tracks, each comprising at least one stationary beat timing mark and at least one moving beat timing mark repeatably moving along the respective rhythm track at a respective uniform speed.

21. The apparatus of claim 14 further comprising:
the trial further comprising:
providing a correct rhythm beat timing indicator on a respective stationary beat timing mark when the user perception indication is coincident with the stationary beat timing mark.

22. the apparatus of claim 14 further comprising:
the plurality of rhythm tracks comprising a left hand rhythm track and a right hand rhythm track; and
the trial further comprising:
providing a correct rhythm beat timing indicator on a respective stationary beat timing mark when user perception indication is coincident with the stationary beat timing mark on one of the respective right hand rhythm track and left hand rhythm track.

23. The apparatus of claim 14 further comprising:
the user computing device further configured to:
eliminate the moving beat timing mark;
receiving via the user interface input a perception indication from the user that the user perceives a beat timing being coincident with a stationary beat timing mark to occur.

24. The apparatus of claim 14 further comprising:
the user computing device further configured to:
determine that the performance of the user has reached a preselected accuracy threshold;
display for the next and subsequent trials a visual indicator that the user scoring has been advanced by a selected multiple.

25. The apparatus of claim 24 further comprising:
including, via the user computing device, an audio indication that the user scoring has been advanced by the selected multiple.

26. The apparatus of claim 25 wherein the preselected accuracy threshold comprises a threshold accuracy level maintained by the user over a selected period of time.

27. The apparatus of claim 26 further comprising:
the user computing device configured to:
maintain the scoring being advanced by the selected multiple while the user continues to achieve the accuracy threshold.

28. A machine readable medium containing instructions that, when executed by a computing device, cause the computing device to perform a method, the method comprising:
providing musical rhythm training comprising at least one trial comprising:
displaying on a user interface display a rhythm track, comprising at least one stationary beat timing mark and at least one moving beat timing mark repeatably moving along the rhythm track at a uniform speed;
receiving a perception indication input from the user that the user perceives the moving beat timing mark to be coincident with a stationary beat timing mark; and
providing an indicator that the perception indication of the user is correct or not correct.

\* \* \* \* \*